*US006905685B2*

United States Patent
Kwon

(10) Patent No.: US 6,905,685 B2
(45) Date of Patent: Jun. 14, 2005

(54) METHODS OF USING ANTIBODIES TO HUMAN RECEPTOR PROTEIN 4-1BB

(76) Inventor: Byoung S. Kwon, 812 Mountain Ash, Carmel, IN (US) 46033

( * ) Notice: Subject to any disclaimer, the term of this patent is extended or adjusted under 35 U.S.C. 154(b) by 627 days.

(21) Appl. No.: 09/877,338

(22) Filed: Jun. 8, 2001

(65) Prior Publication Data

US 2004/0091476 A1 May 13, 2004

Related U.S. Application Data

(60) Division of application No. 09/007,097, filed on Jan. 14, 1998, now Pat. No. 6,303,121, which is a continuation-in-part of application No. 08/409,851, filed on Mar. 23, 1995, now abandoned, and a continuation-in-part of application No. 08/122,796, filed on Sep. 16, 1993, now abandoned.

(51) Int. Cl.[7] .................... A61K 39/395; C07K 16/00; C07K 14/00
(52) U.S. Cl. .................. 424/138.1; 530/387.1; 530/388.1; 530/289.1; 530/350; 424/139.1
(58) Field of Search ................ 424/139.1, 138.1; 530/387.1, 388.1, 389.1, 350

(56) References Cited

U.S. PATENT DOCUMENTS

| 5,674,704 A | 10/1997 | Goodwin et al. | ........... 435/69.1 |
| 5,928,893 A | 7/1999 | Kang et al. | ........... 435/69.1 |

FOREIGN PATENT DOCUMENTS

| WO | 96/29348 | 9/1996 | ........... C07K/16/00 |
| WO | 97/33898 | 9/1997 | ........... C07H/21/00 |

OTHER PUBLICATIONS

Bressler et al., "Anti–CD2 Receptor Antibodies Activate the HIV Long Terminal Repeat in T Lymphocytes", J. Immunology 1991 174(7) :2290–2294.
Carthew et al., "seven in absentia, a Gene Required for Specificaiton of R7 Cell Fate in the Drosophila Eye", Cell 1990 63:561–577.
Defrance et al., "Interleukin 10 and Transforming Growth Factor β Cooperate to Induce Anti–CD40–activated Naive Human B Cells to Secrete Immunoglobulin A", J. Exp. Med. 1992 175:671–682.
Haskins et al., "The Major Histocompatibility Complex–Restricted Antigen Receptor on T Cells", J. Exp. Med. 1983 157:1149–1169.
Kwon et al., "Isolation and initial characterization of multiple species of T–lymphocyte subset cDNA clones", Proc. Natl. Acad. Sci. USA 1987 84:2896–2900.
Mallett et al., "A new superfamily of cell surface proteins related to the nerve growth factor receptor", Immunology Today 1991 12(7) :220–223.
Maraskovsky et al., "Co–engagement of CD3 with LFA–1 or 1CAM–1 adhesion molecules enhances the frequency of activation of single murine CD4+ and CD8+ T cells and induces synthesis of IL–3 and IFN–γ but not IL–4 or IL–6", International Immunology 1992 4(4):475–485.

Mueller et al., "Clonal Expansion Versus Functional Clonal Inactivation: A Costimulatory Signalling Pathway Determines the Outcome of T Cell Antigen Receptor Occupancy[1]", Ann. Rev. Immunol. 1989 7:445–480.
Noelle et al., "Cognate interactions between helper T cells and B Cells", Immunology Today 1990 11(10):361–368.
Van Lier et al., "Tissue Distribution and Biochemical and Functional Properties of Tp55 (CD27), A Novel T Cell Differentiation Antigen", J. Immunology 1987 139(5):1589–1596.
Debenedette et al., "Costimulation of CD38–T Lymphocytes by 4–1BB Ligand", J. Immunology 1997 158(2):551–559.
Kwon et al., "cDNA sequences of two inducible T–cells genes", Proceedings of the National Academy of Sciences 1989 86(6):1963–1967.
Melero et al., "Monoclonal Antibodies Against the 4–1BB T–cell Activation Molecule Eradicate Established Tumors", Nature Medicine 1997 3(6):682–685.
Schwartz et al., "A receptor induced by lymphocyte activation (ILA) :a new member of the human nerve–growth–factor/tumor–necrosis–factor receptor family", Gene 1993 134:295–298.

(Continued)

*Primary Examiner*—Janet Andres

(57) ABSTRACT

Disclosed herein are the methods of using the H4-1BB protein, ligands to this protein, and various mAbs either directed against H4-1BB or other molecules that can be used therapeutically. The nature and importance of the H4-1BB molecule provides the ligands and related co-stimulatory molecules the ability to enhance or suppress T-cell activation and proliferation. By treating T-cells that have expressed receptor protein H4-1BB with one of the four anti-H4-1BB monoclonal antibodies disclosed herein activation or inhibition of the immune response is seen. Also disclosed herein is cDNA for the human receptor H4-1BB. The cDNA of the human receptor H4-1BB is about 65% homologous to the mouse cDNA 4-1BB and was isolated by using probes derived from murine cDNA 4-1BB. A fusion protein for detecting cell membrane ligands to human receptor protein H4-1BB was developed. It comprises the extracellular portion of the receptor protein H4-1BB and a detection protein, alkaline phosphatase, bound to the portion of the receptor protein H4-1BB. B-cells that have expressed a ligand to receptor protein H4-1BB can be treated with cells that have expressed receptor protein H4-1BB and B-cell proliferation may be induced. The use of H4-1BB to block H4-1BB ligand binding has practical application in the suppression of the immune system during organ transplantation or against autoimmune diseases including diabetes, rheumatoid arthritis, and lupus. Other applications of this technology include the development of therapeutic methods for the treatment of HIV-1 infected individuals, and the treatment of cancerous tumors.

8 Claims, 3 Drawing Sheets

OTHER PUBLICATIONS

Shuford et al., "4–1BB Costimulatory Signals Preferentially Induce CD8+ T Cells Proliferation and Lead to the Amplification In Vivo of Cytotoxic T Cell Responses", J. Experimental Medicine 1997 186(1):47–55.

Alderson, M.R., et al., "Molecular and Biological Characterization of Human 4–1BB and its Ligand", *Eur. J. Immunol.*, *24*, pp. 2219–2227, (1994).

Debenedette, M.A., et al., "Costimulation of CD28–T Lymphocytes by 4–1BB Ligand", *The Journal of Immunology*, *158* (2), pp. 551–559, (1997).

Melero, I., et al., "Monoclonal Antibodies Against the 4–1BB T–cell Activation Molecule Eradicate Established Tumors", *Nature Medicine*, *3* (*6*), pp. 682–685, (Jun. 1997).

Pollok, K.E., et al., "Inducible T Cell Antigen 4–1BB", *J. Immunol.*, *150* (*3*), pp. 771–781, (1993).

Shuford, W.W., et al., "4–1BB Costimulatory Signals Preferentially Induce CD8+ T Cells Proliferation and Lead to the Amplification In Vivo of Cytotoxic T Cell Responses", *The Journal of Experimental Medicine*, *186* (*1*), pp. 47–55, (1997).

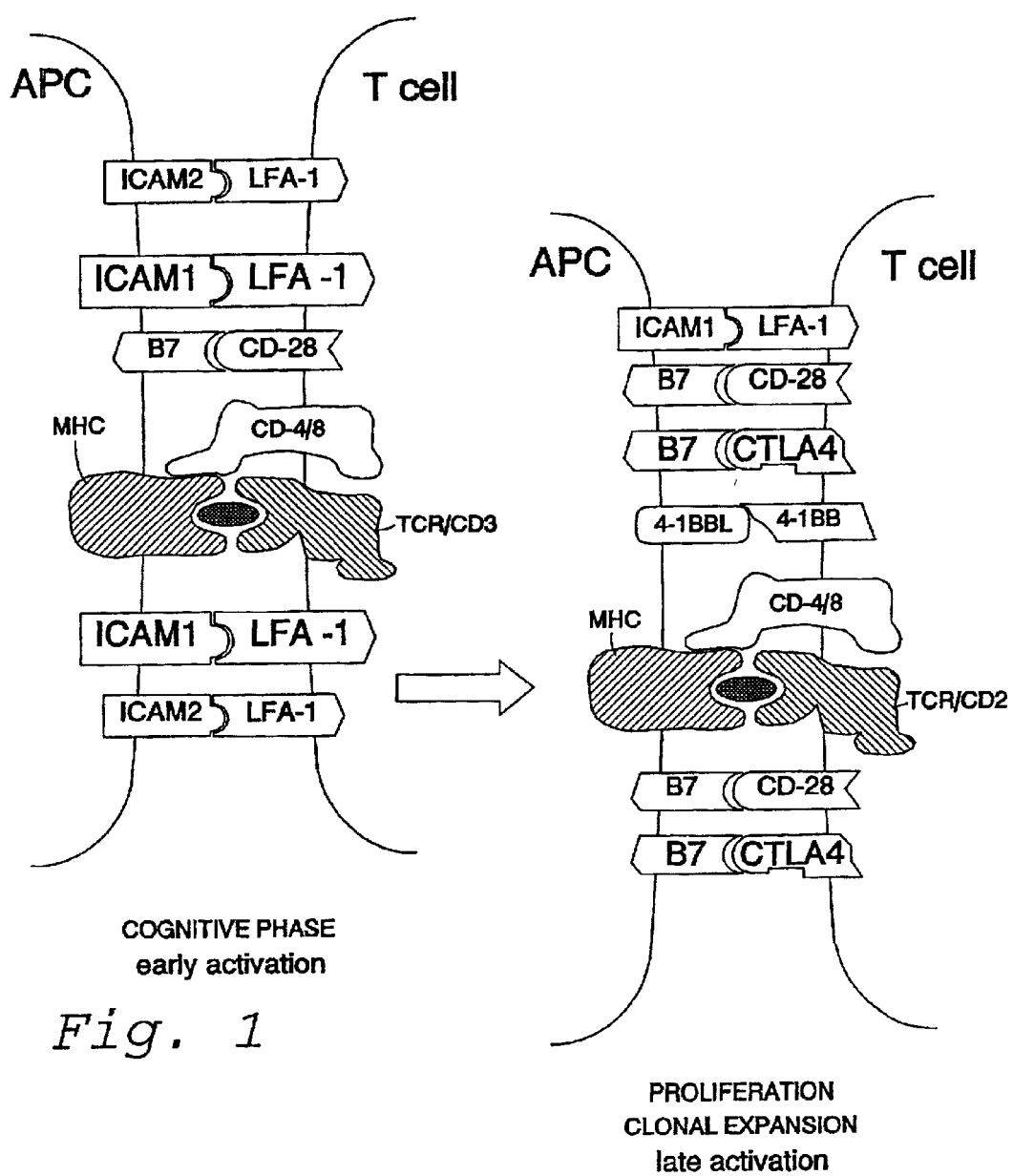
Fig. 1 — COGNITIVE PHASE early activation
Fig. 2 — PROLIFERATION CLONAL EXPANSION late activation

NORMAL T-CELL ACTIVATION PATHWAY

BLOCKING STEPS IN T-CELL ACTIVATION PATHWAY

METHODS OF USING ANTIBODIES TO HUMAN RECEPTOR PROTEIN 4-1BB

CROSS REFERENCE TO RELATED APPLICATIONS

This application is a divison of U.S. application Ser. No. 09/007,097, filed Jan. 14, 1998, now U.S. Pat. No. 6,303,121, which is a continuation-in-part of application Ser. No. 08/409,851 filed Mar. 23, 1995 now abandoned, and of application Ser. No. 08/122,796 filed Sep. 16, 1993 now abandoned.

The subject matter described herein was in part a subject invention of NIH Grants Nos. IR23AI23058-03, R01 AI-28175, R01 DE-12156, and P60 KD20542 of which the present inventor was the Principal Investigator and either the Donald Guthrie Foundation for Medical Research Inc. of Guthrie Square, Sayre; Pa. 18849–1669 or Indiana University School of Medicine of Indianapolis, Ind. 46202, was the Grantee.

FIELD OF THE PRESENT INVENTION

The present invention relates to the therapeutic and scientific uses for the human H4-1BB protein, its ligands, and the development of monoclonal antibodies that recognize and bind the H4-1BB receptor protein.

BACKGROUND OF THE PRESENT INVENTION

The immune system of humans and other species require that white blood cells, which include phagocytes, T lymphocytes and B cells, be made in the bone marrow. The phagocytes include macrophage cells which scavenge unwanted materials, such as virus proteins or bacterial cell walls from the system. The lymphocytes include helper T cells, killer T cells and B cells, as well as other types of cells, including those categorized as suppressor T cells. The B cells produce the antibodies. The killer T cells physically destroy target cells and the helper T cells facilitate the whole process. The complexities of the immune system and its function is facilitated, at least in part, by the lymphokines.

Lymphokines are signal transduction proteins by which the immune cells communicate with each other. Scientists have been able to produce them in sufficient quantities for therapeutic use against immunologic diseases. There are many known lymphokine proteins and they include the interferons, interleukins-1,2,3,4,5,6,7, colony-stimulating factors, lymphotoxin, tumor necrosis factor and erythropoietin, as well as others.

Interleukin 1 (IL-1), secreted from macrophages activates the helper T cells and acts to raise body temperature, causing fever, which enhances the activity of the immune cells. The activated helper T cells produce Interleukin 2 (IL-2), which in turn stimulates the helper and killer T cells to grow and divide. The helper T cells also produce another lymphokine, B cell growth factor (BCGF), which causes B cells to multiply. As the number of B cells increases, the helper T cells produce another lymphokine known as the B cell differentiating factor (BCDF), which instructs some of the B cells to stop replicating and start producing antibodies.

T cells also produce gamma interferon (IF), which is similar to Interleukin 2 in that it has multiple effects. Gamma interferon helps activate killer T cells, enabling them to attack the invading organisms. Like BCGF, gamma interferon increases the ability of the B cells to produce antibodies. IF also keeps the macrophages at the site of the infection and helps the macrophages digest the cells they have engulfed. Gathering momentum with each kind of lymphokine signal between the macrophages and the T cells, the lymphokines amplify the immune system response such that the virus protein, an infected cell, or other foreign matter is overwhelmed and removed from the system. There are many lymphokines, maybe a hundred or more, which participate in the complex web that is the immune process. Many lymphokines and their precise effects remain unknown.

Lymphokine activities are produced when a certain lymphokine binds to its specific receptor on the surface of a target cell. Among scientists there is widespread use of cloned cell lines for production of lymphokines and their receptors. The isolation of lymphokine and lymphokine receptor messenger ribonucleic acid (mRNA) has become a common technique. The mouse receptor protein, 4-1BB, was isolated and identified based on specific expression of the T cell genes using a technique identified by the present inventor in a prior publication (*Proc. Natl. Acad. Sci. USA*, 84, 2896–2900, May 1987, Immunology). The protocol reported in this publication can be used by scientists to detect virtually all of the lymphokines. The method is designed to detect virtually all mRNA expressed differentially. Importantly, the mRNA sequences of immune cells are expressed differentially as they relate to T cells generally, and to the killer T cells specifically. Even though the level of expression is low and the quantity of the lymphokine and its receptor protein is low, this expressed mRNA can be detected and isolated. The present inventor believes that the analysis described in the above-identified publication can reveal biologically important molecules such as lymphokines and their receptors because there are many indications that biologically important or active molecules are initiated by cellular signals induced by very scarce message molecules (i.e., IF, interleukins, Map Kinase Kinase, etc.).

Most T cell factors have been classically identified by recognizing biologic activities in assays, and thereafter purifying the protein information. An alternative approach is to isolate putative T cell genes based upon specific expression, insert them into an appropriate expression vector, and then demonstrate the function of the unknown isolated protein. Using the aforesaid modified differential screening procedure, the present inventor cloned a series of T cell subset-specific complementary deoxyribonucleic acid (cDNA) from cloned helper T lymphocyte (HTL) L2 cells, and cloned cytolytic T lymphocytes (CTL) L3.

T cells are critically important in long-term acquired immunity, providing protection against viral, bacterial and parasitic infection. T cells are activated when they encounter a peptide from the invading pathogen in context with self-MHC (Major Histocompatibility Complex) via the T cell's own T cell receptor (TCR) complex and other co-stimulatory molecule(s), such as CD-28, or CD-3. Without the engagement of the other co-stimulatory molecule(s), the T cell is rendered anergic (Vassali et al., *PNAS*, 1979). To date, the best-characterized co-stimulatory molecule has been CD-28. More recently, however, other cell-surface molecules have been suggested to play a co-stimulatory role, such as the molecule 4-1BB. The 4-1BB protein is a –55 kDa homodimeric molecule expressed on activated T cells in the mouse, and is a member of the Nerve Growth Factor receptor (NGFR)/Tumor Necrosis Factor receptor (TNFR) gene super family (Haskins et al., *J. Exp. Med.*, 1983). This family is characterized by the presence of cysteine-rich motifs in the extracellular domains. Other members of this family include NGFR, B cell activation molecule CD40, the T cell activation molecule OX-40 in rat and CD27, the two receptors for tumor necrosis factor (TNF) called TNFR-1 and TNFR-11, the apoptotic-inducing protein Fas, and CD-30 which plays a role in the regulation of cellular growth and transformation.

Some of these members have been shown to play important roles in human immunodeficiency virus-1 (HIV-1) infection, including CD4+ T cell proliferation, apoptosis and virus replication. The presence of high serum levels of CD30 has become a predictor of progression to acquired immunodeficiency syndrome (AIDS), although no circulating CD30 cells have been found in HIV-1 seropositive individuals. The expression of HIV-1 was induced by triggering CD30 of HIV-1 infected CD4+ T cells through a nuclear factor-κβ (NF-κβ)-dependent pathway. In HIV-1 individuals, high levels of Fas expression were observed in peripheral blood lymphocytes. Fas production was found to trigger or induce marked apoptosis of T lymphocytes, which might contribute to the CD4+ T cell depletion by HIV-1 infection. The ability of CD4+ T cells to express the CD40 ligand after in vitro stimulation is not impaired because of HIV-1 infection, but CD40/CD40 ligand interaction regulates HIV-1 replication of B cells in vitro. CD27 signaling enhanced proliferative response of T cells to the normal extent in HIV-1-infected individuals.

In the experiments that led to the development of this invention, a series of T cell subset-specific cDNAs were isolated from cloned murine T-cells by employing a modified differential screening procedure. The nucleotide sequence and expression properties of some of the cDNA species have been reported. One of the genes not previously characterized, which encodes mouse receptor protein 4-1BB, was studied further. These studies have led to the isolation of the human homologue to 4-1BB, H4-1BB, as well as to a series of monoclonal antibodies capable of binding the H4-1BB receptor protein and acting thereby as agonists or antagonists of H4-1BB.

T cells interact with components of the extracellular matrix (ECM) through members of the integrin family after transendothelial migration during homing to sites of inflammation. Integrin molecules are very late antigens (VLA's) in a family of cell surface receptors that mediate the adhesion of cells to ECM proteins as well as other cells. The heterodimeric integrins comprising of various alpha and beta subunits, act as a transducing mechanism of extracellular signals. Regulation of integrin function is utilized by T cells and other leukocytes for rapid adhesion following activation of the cells.

The major factors known so far to affect the differentiation of the T cells are the lymphokines (also referred to as cytokines), such as IL-2 and IL-4. In vitro and in vivo studies with transgenic mice have demonstrated that IL-2 induces the development of the Th1 subset of T cells by priming them for efficient IF production and preventing development of IL-4-producing cells. Previously however, it was unknown how their interactions worked to direct the amplification of the immune response and development of the Th1 or Th2 subset of T cells.

Specific immune responses are governed by the recognition of antibodies to foreign antigens. Antibodies form a family of structurally related glycoproteins and confer, generally to the organism producing them, the protective effect of cell-mediated immunity. Antibodies are produced by B-lymphocytes and are bound to the cell membrane, functioning as B cell receptors for antigens. Antibodies are also secreted by B cell progeny that differentiate in response to stimulation by antigens. A specific antigen will trigger the complementary B lymphocyte(s) to proliferate and differentiate into effector cells, which then eliminate the antigen. Each lymphocyte produces an antibody of a particular specificity, and thus immune responses are very specific for distinct antigens. The portion of the antigen recognized by T and B lymphocytes are called epitopes or determinants.

The development of techniques to produce virtually unlimited amounts of a single (monoclonal) antibody for a specific antigenic epitope has had an enormous impact on clinical immunology. To produce a monoclonal antibody (mAb) of known specificity, a mouse can be injected with a particular antigen, such as a receptor protein and the spleen B lymphocytes (that produce the antibody against the protein) can be fused via somatic cell hybridization to a myeloma (lymphocyte tumor) to produce an immortal cell line to create a hybridoma. This is done because normal B-lymphocytes cannot grow indefinitely, yet when fused with the myeloma, the resulting hybridoma produces a virtually endless supply of a specific monoclonal antibody. Selection techniques have been developed to ensure that only the fused cells continue to grow. Each hybridoma cell is specific for only one antigenic determinant. If several different antibody-producing hybridomas are produced, each hybridoma clone of an individual B lymphocyte will secrete an antibody for only one surface antigenic determinant. To determine which mAbs specifically bind to the protein receptor, or which has a desired activity (e.g., the mAb acts as an agonist, antagonist, or has the most specific binding to a critical epitope), the hybridomas can be screened with an ELISA (enzyme-linked immunosorbent assay).

Monoclonal antibodies have numerous-applications: 1) The hybridoma can produce large quantities of specific antibodies that are normally either unavailable in small quantities or not available at all; 2) the hybridoma can be directed to produce antibodies against a single antigen determinant which, for complex antigens, may be normally very difficult; 3) pure antibodies can be obtained against antigens that cannot be purified; 4) immunodiagnosis of infectious and systemic diseases by detecting specific antigens circulating in tissues or using monoclonal antibodies in immunoassays; 5) characterization of protein receptors and the role they play in the transition from a naive to a memory T cell; and 6) blocking or enhancing immune response or activation.

The invention below presents uses for the H4-1BB protein, its ligands, antibodies thereto and other co-stimulatory molecules that can be used therapeutically in the treatment of cancer and HIV-1.

SUMMARY OF THE PRESENT INVENTION

The present invention includes the human receptor protein H4-1BB and the cDNA gene encoding for human receptor protein H4-1BB. The nucleotide sequence of the isolated cDNA is disclosed herein along with the deduced amino acid sequence. The cDNA gene identified as pH 4-1BB was deposited at the Agricultural Research Service Culture Collection and assigned the accession number: NRRL B21131

The cDNA, including its fragments and derivatives, can be used as a probe to isolate DNA sequences encoding for proteins similar to the receptor protein. The cDNA of the human receptor, H4-1BB, was isolated by using probes derived from cDNA 4-1BB. The cDNA gene identified as p4-1BB was deposited at the American Type Tissue Culture Collection at 10801 University Boulevard, Manassas, Va.

20110-2209 under ATCC NO.: 67825. The present invention also provides an antibody specific for H4-1BB. One exemplary hybridoma which secretes such an antibody was deposited at the American Type Tissue Culture Collection on Mar. 10, 1995 under ATCC No. HB-11860.

The human receptor protein H4-1BB can be produced by: 1) inserting the cDNA of H4-1BB into an appropriate expression vector, 2) transfecting the expression vector into an appropriate transfection host, c) growing the transfected hosts in appropriate culture media and d) purifying the receptor protein from the culture media. The protein and fragments and derivatives can be used: 1) as a probe to isolate ligands to human receptor protein H4-1BB, 2) to stimulate proliferation of B-cells expressing H4-1BB ligands, or 3) to block H4-1BB ligand binding.

B-cell proliferation can be induced by treating B-cells that have expressed a ligand to receptor protein H4-1BB with cells that have expressed receptor protein H4-1BB. The use of H4-1BB protein, H4-1BB ligand protein, or fragments of the proteins, to block H4-1BB ligand binding has practical application in the suppression of the immune system during organ transplantation.

Monoclonal antibodies generated against H4-1BB can be used to enhance or suppress T-cell proliferation and activation by treating T-cells that have expressed receptor protein H4-1BB with an anti-H4-1BB monoclonal antibodies. To enhance immune reaction antibodies which act as agonists can be generated, to suppress T-cell proliferation and/or activation antibodies which act as antagonists can be generated. To this end, four monoclonal antibodies have been developed for use. The monoclonal antibodies BBK-1 and BBK-4 are agonists to receptor protein H4-1BB, while monoclonal antibodies BBK-2 and BBK-3 are antagonists to receptor protein H4-1BB, and can be used to either upregulate the immune system or suppress its activity. Some tumors are potentially immunogenic but do not stimulate an effective anti-immune response in vivo. Tumors may be capable of delivering antigen-specific signals to T cells, but may not deliver the co-stimulatory signals necessary for full activation of T cells. A monoclonal antibody generated against H4-1BB (e.g. an agonist) is capable of eradicating tumors with low immunogenicity by providing for the full activation, enhancement, and/or proliferation of T-cells. Moreover, an anti-H4-1BB mAb agonist has great utility in assessing the role of the 4-1BB receptor protein in the transition from naive to memory T-cells. Cross-linking of the 4-1BB with an anti-H4-1BB mAb agonist, such as BBK-1 or BBK-4 will produce the effects similar to the binding of the 4-1BB ligand to 4-1BB.

A mAb agonist H4-1BB can also be used to interfere with H4-1BB and H4-1BB ligand binding. By interfering with ligand binding, as with the use of an anti-H4-1BB mAb antagonist BBK-2, and BBK-3, the immune responses will be suppressed. In this context, diseases that would benefit from the therapeutic use of such a mAb include rheumatoid arthritis, systemic lupus erythematosus, and diabetes. Alternatively, this type of molecule is useful in organ transplantation to suppress immune system mediated rejection of transplanted tissue.

A fusion protein can detect cell membrane ligands to human receptor protein, H4-1BB. A fusion protein of the present invention comprises the extracellular portion of the receptor protein H4-1BB and a detection protein (alkaline phosphatase) or Fc portion of an $IgG_1$ bound to the portion of the receptor protein H4-1BB. In addition, this disclosure demonstrates that co-engagement of CD28 with 4-1BB promoted type 1 effector T cell development. The 4-1BB signal regulated CD28 mediated cytokine production profiles in two ways, enhancing type 1 and, at the same time, suppressing type 2 cytokine (lymphokine) production. The 4-1BB-mediated co-stimulation also induced γ-interferon (IF) production in Th1 cells. The expression of 4-1BB was subset-specific, being detected predominantly on IF-producing, but not on IL-4-producing cells. Moreover, it was determined that 4-1BB and CD30 expression were mutually exclusive, representing type 1 and type 2 subsets, respectively. The co-engagement of 4-1BB with CD28 enhanced long-term cell survival for cells susceptible to apoptosis induced by repeated TCR activation. Therefore, it was demonstrated that 4-1BB and CD30 interplay to regulate the balance between type 1 and type 2 T cell subsets, and the polarization of the immune response. Therapeutically, they can be used to achieve opposite effects.

This invention presents data, which demonstrates that there is a functional correlation between 4-1BB and CD28 in T cell adhesive responses. The inventors disclose herein that 4-1BB can induce of cell adhesion. Enhanced cell adhesion through the presence 4-1BB signal or agonist results in a maximal T cell activation in response to repeated exposure to sub-optimal concentrations of anti-CD3 and anti-CD28. Thus, 4-1BB effects were attributed by its ability in reducing the threshold of anti-CD3 concentration needed to repeatedly activate primary T cells. Therefore the degree of cell adhesion in response to anti-4-1BB correlated with the 4-1BB expression levels, and correspondingly effects the therapeutic use of these molecules.

The level of 4-1BB-expressing and the percentage of 4-1BB-expressing T cells was higher in HIV-1 positive individuals than in the HIV-1 controls (P<0.01). 4-1BB signal cooperated with CD28 to induce HIV-1, and CD4+ T cell proliferation. In addition, cross-linking 4-1BB with agonistic monoclonal antibodies enhanced HIV-1 replication both in primary stimulation and secondary re-stimulation of CD4+ T cells from HIV-1 individuals. Thus, 4-1BB is involved in the activation of HIV-1 replication from latently infected CD4+ T cells, and the 4-1BB co-stimulatory pathway can be the target of therapeutic intervention. If the pathway of HIV-1 infection is disturbed at the early stages of the infection, through the use of H4-1BB antibodies a lower virus load will result. Moreover, the increased 4-1BB expression on CD8+ T cells is noteworthy because it is correlated with the degree of immunodeficiency in HIV-1 infection, cross-linking 4-1BB on CD8+ T cells will induce enhanced cytotoxic activity against HIV-1 infected CD4+ T cells.

An object of the present invention is to teach a fusion protein comprising the extracellular portion of H4-1BB and a detection protein.

Another object of the present invention is to teach the method of constructing a monoclonal antibody against H4-1BB.

BRIEF DESCRIPTIONS OF THE FIGURES

FIG. 1 illustrates the molecules involved in the cognitive phase of T-cell activation.

FIG. 2 illustrates the molecules involved in the clonal expansion of Tcells occurring in the late portion of T-cell activation.

DETAILED DESCRIPTION

Figure 3:
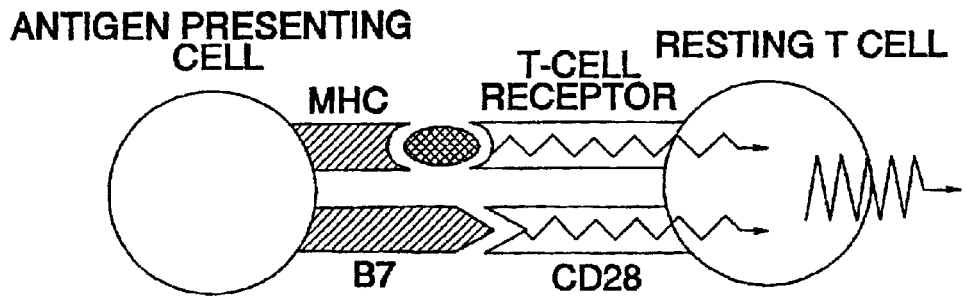
FIG. 3 illustrates the resting portion of a normal T-cell activation pathway.

The following description teaches the isolation of 4-1BB and its human homologue, H4-1BB, the preparation of the peripheral blood cells, including the antibodies and reagents used, the production of fusion protein, immunization, and the production of monoclonal antibodies acting as either agonists or antagonists of H4-1BB. Also disclosed is the therapeutic use of: 4-1BB, antibodies to it, its ligands, and immunoprecipitation studies.

Isolation and Characterization of Mouse Receptor 4-1BB

U.S. application Ser. No. 08/012,796 discloses the nucleotide sequence and the deduced amino acid sequence of the mouse receptor 4-1BB. The transcript of 4-1BB was inducible by concanavalin A in mouse splenocytes, T cell clones, and hybridomas. The expression of 4-1BB transcripts was inhibited by cyclosporin A. The 4-1BB mRNA was inducible by antigen receptor stimulation but was not inducible by IL-2 stimulation in the cloned T-cells (1). The 4-1BB cDNA encodes a peptide of 256 amino acids containing a putative leader sequence, a potential membrane anchor segment, and other features of known receptor proteins. Therefore, the expression pattern of 4-1BB resembles those of lymphokine mRNAs while the sequence appeared consistent with those of receptor proteins.

The major species of 4-1BB on the cell surface appears to be a 55-kDa dimer. 4-1BB also appears to exist as a 30-kDa monomer and possibly as a 110-kDa tetramer. Since these 4-1BB species were immunoprecipitated from a homogeneous population of cells (T-cell clone f1), all forms potentially co-exist on each cell. Peptide digests from the 4-1BB monomer and dimer are needed to determine whether 4-1BB exists as a homodimer on the cell surface. A variety of cell surface receptors such as the insulin receptor (Ebina et al., 1985), the B cell surface immunoglobin receptor (Vassali et al.,), the T cell Ag receptor (Haskins et al., 1983), the CD-28 co-stimulatory receptor (Lesslaver et al., 1986), and the CD27 T-cell antigen (Van Lier et al., 1987) are composed of disulfide-bonded subunits. Receptor dimerization may be required for ligand binding and subsequent cell signal transduction.

4-1BB is not expressed on resting T cells but is inducible by activators which deliver a complete growth stimulus to the T cell. The combination of phorbol myristate acetate (PMA) and ionomycin is capable of mimicking those signals required for T cell proliferation. Although PMA or ionomycin alone induced 4-1BB mRNA, the combination of PMA and ionomycin resulted in optimal 4-1BB expression. Furthermore, the expression of 4-1BB was not transient. When purified splenic T cells were stimulated with immobilized anti-CD3, 4-1BB mRNA was expressed and this expression was maintained for up to 96 hrs post-stimulation. Cell-cycle analysis will be required to confirm that 4-1BB is expressed throughout cell-cycle progression.

4-1BB is structurally related to members of the nerve growth factor receptor super-family. Although these receptors possess structurally similar ligand-binding properties (cysteine-rich regions), the cytoplasmic domains of these proteins are non-conserved which could allow for diversity in transmembrane signaling. Some members of this family are involved in the T or B cell activation process. There are in vitro functional data on the OX-40, CD40 and CD27 antigens. Antibodies against the OX-40 augment the T-cell response in a mixed lymphocyte reaction and antibodies against CD40 enhance B-cell proliferation in the presence of a co-activator, such as PMA or CD20 antibodies, and synergizes with IL-4 in vitro to induce B-cell differentiation and to generate long-term normal B cell lines. One monoclonal antibody, anti-1A4, which recognizes an epitope on the CD27 molecule inhibited calcium mobilization, IL-2 secretion, helper T cell function, and T cell proliferation. On the other hand, CLB-CD27/1, another anti-CD27 mAb enhanced proliferation of human T cells stimulated with phytohemagglutinin (PHA) or anti-CD3 mAb. These results indicate that the CD27 molecule plays an important role in T cell activation. Except for TNFR's, NCFR and CD40, the ligands or cell-surface molecules to which the members of the superfamily bind are not yet identified. Identification and characterization of the ligands to which the receptors bind will be helpful in better defining the physiologic role of 4-1BB.

To ascertain whether cell surface 4-1BB could contribute to T cell activation, the anti-4-1BB 53A2 was used as an antagonist to 4-1BB. The resulting data suggest that 4-1BB does in fact have the potential to function as an accessory signaling molecule during T cell activation and proliferation. The addition of soluble 53A2 to purified splenic T cells stimulated with immobilized anti-CD3 resulted in an amplification of $^3$H thymidine incorporation compared to T cells stimulated with anti-CD3 alone. This pattern of enhancement ranged from 2- to 10-fold in three independent experiments.

In the original two signal model of Bretcher and Cohn, they proposed that signal 1, the occupancy of the T cell antigen receptor (TCR), resulted in inactivation of the T cell in the absence of signal 2, which is provided by accessory cells. This has since been confirmed by a variety of studies (Moeller et al., 1989). The identification of the accessory cell CD28 as a potent co-stimulatory receptor on T cells was a significant contribution in beginning to characterize the accessory signal(s) required for optimal T cell proliferation. It is possible that other cell surface molecules may contribute to these co-stimulatory activation requirements.

The biochemical signals delivered through 4-1BB indicate that there is a putative $p56^{lck}$ tyrosine kinase-binding domain in its cytoplasmic tail. It was later determined that $p56^{lck}$ tyrosinase kinase binds to 4-1BB. It will also be worthwhile to determine if 4-1BB-mediated signaling can regulate genes such as IL-2 and IL-2 receptor, whose expression is required for T cell activation and subsequent proliferation.

The precise functions of member of the Nerve Growth Factor Receptor (NGFR) superfamily appear to be diverse. An emerging them of inquiry concerns the ability of these molecules to maintain the responsiveness or viability of the particular cell type in which they are expressed. For instance, NGF is absolutely required for viability of neurons in vitro and in vivo (Yamori et al., 1992). The cross-linking of CD40 by soluble antiCD40 monoclonal antibody blocks germinal center centrocytes from undergoing apoptosis in vitro. Signals delivered through CD40 may also aid in maintenance of responsiveness to differentiation factors. The ligation of CD40 with anti-CD40 F(ab')$_2$ fragments in the presence of IL-4 induced large increases in IgE synthesis. Also, anti-CD40 activated naive B cells treated with IL-10 and transforming growth factor-β became committed to IgA secretion (DeFrance et al., 1992). In addition to sharing the molecular characteristics with the NGFR superfamily, it was noted that the 4-1BB contained a putative zinc finger structure similar to that of the yeast elF-2b protein. 4-1BB also shares a conserved region with the sina seven in absentia of Drosophila Melanogaster, which is required for correct photoreceptor cell development (Carthew and Rubin, 1990). That particular region is also similar to the protein product of the DGl7 gene of Dictyosteliun, whose expression is specifically induced during aggregation by cyclic adenosine monophosphate (cAMP).

This region forms the pattern of C—$X_2$—C—$X_9$—C—$X_3$—H—$X_3$—C—X—C (SEQ ID NO:9); and the cysteines and histidine are conserved in a similar space in 4-1BB, sina, and DGl7 proteins. Ten of 24 amino acids between the 4-1BB and sina proteins are identical; 3 of 24 are conservative substitutes. The conserved pattern suggests that these amino acids are functionally important. The sina protein is localized in the nucleus, suggesting that it has a regulatory function in cells. The fact that the amino acid sequence of 4-1BB contains features like a zinc finger motif, a nuclear protein, and a receptor domain suggests that 4-1BB may play diverse roles during cellular proliferation and differentiation.

In addition, 4-1BB may represent another cell-surface molecule involved in T cell-antigen presenting cell (APC) interactions. The 4-1BB-alkaline phosphatase (4-1BB-AP) fusion protein specifically bound to mature B-cell lines, anti-IF-activated primary B cells, and mature macrophage-cell lines. 4-1BB-AP bound at low or insignificant levels to immature B-and macrophage-cell lines, T cell clones, T cell lines, primary culture T cells, and various non-lymphoid-cell lines. Since 4-1BB-AP binds to mature B cells and macrophages, it is possible that signals delivered upon 4-1BB binding may modulate APC functions in some way. This possibility remains to be explored.

Chalupny et al., proposed that 4-1BB Rg, a fusion protein consisting of the extracellular domain of 4-1BB and the Fc region of human IgG, bound to the extracellular matrix (ECM). The highest level of 4-1BB Rg binding was to human vitronectin. The inventors performed an ELISA to test this possibility using 4-1BB-AP and human vitronectin (Yelios Pharmaceuticals/GIBCO-BRL, Grand Island, N.Y.) immobilized at 0.007 mg, with 10 mg per well on microtiter plates. No binding of 4-1BB-AP based on AP activity was observed. To rule out the possibility that 4-1BB-AP was binding to proteins extrinsically attached to the cell surface (possible extracellular matrix components), B-cell lymphomas were washed in acid conditions prior to the binding assay. 4-1BB-AP still bound specifically to mature B-cell lymphomas. It is still to be determined whether a 4-1BB-ligand specifically expressed on B cells and macrophages exists, and whether 4-1BB-AP may bind to the ECM under particular binding conditions. It is possible that the ECM could facilitate the binding of 4-1BB to a specific cell-surface ligand.

B cells and helper T cells interact with each other through receptors on B cells binding to their specific counter-receptors on T cells. This interaction results in a cascade of biochemical signaling relays between the two cell types. As this interaction proceeds, these cells become committed to enter the S-phase of the cell cycle. Initial interactions between TCR and CD4+ on T cells, and processed antigen-MHC II on B cells, do not result in B cells capable of entering the cell cycle (Noelle and Snow et al., 1990). However, studies from in vitro systems suggest that once T cells are stimulated, they express newly synthesized or modified cell-surface molecules capable of inducing B cells to enter the cell cycle. This T cell function is not antigen-specific or MHC-restricted. In addition, soluble factors are not required for the Th induction of B-cell activation. Once B cells enter the cell cycle, IL-4 induces B cells to progress from $G_1$ to S phase. The ability of activated T cells or T-cell membranes to promote the entry of B cells into the cell cycle can be blocked by either cycloheximide or cyclosporin A treatment. These newly expressed membrane proteins appear to be "lymphokine-like" in their induction characteristics.

4-1BB has expression properties which meet the requirements of a B-cell co-stimulator. 4-1BB is inducible by anti-CD3 or TCR-mediated T-cell stimulation, and its expression is sensitive to cyclosporin A as well as cycloheximide treatment. Interestingly, paraformaldehyde-fixed SF21-4-1BB cells, synergized anti-μ and induced B-cell proliferation. The co-stimulation of splenic B cells by SF21-4-1BB occurred at optimal (10 μg/ml) and sub-optimal (1.0–0.1 mg/ml) doses of anti-μ. The addition of SF21-4-1BB cells to resting B cells, did not result in significant B-cell proliferation. SF21-4-1BB cells did not synergize with tetradecanoylphorbolacetate (TPA) or ionomycin, or sub-optimal concentrations of LPS in inducing B-cell proliferation.

Although the baculovirus system has been used to express large amounts of recombinant soluble proteins, this system may be utilized for the expression of recombinant cell-surface proteins. The baculovirus infection provides a convenient means to express uniformity high levels of recombinant protein on a per cell basis. It is noteworthy, that the addition of SF21 cells alone did not result in significant levels of co-stimulation. This can be a potential problem when using COS- or L-cell lines which can exhibit strong co-stimulation activity on their own.

Another member of the NGFR superfamily, CD40, is expressed on B cells and interacts with gp39, a molecule expressed on activated T cells. The cDNAs encoding the murine and human gp39 proteins have been cloned; this cell surface molecule is a type II membrane protein with homology to tumor necrosis factor. Noelle et al., found that a CD40-immunoglobulin fusion protein, is capable of blocking T cell-induced B-cell proliferation and differentiation in a dose-dependent manner. Armitage et al. have isolated a cDNA for murine gp39 and showed that gp39 could induce B-cell proliferation in the absence of co-stimuli; and result in IgE production in the presence of IL-4-. Hollenbaugh et al., have shown that COS cells transfected with human gp39 can synergize with either TPA or anti-CD20 in inducing human B-cell proliferation and is able to stimulate B cells without a co-stimulator only at low levels. These data indicate that CD40 may be one of the B-cell-surface molecules that transmit signals during physical contact with T cells.

Cell-surface receptors communicate with their external milieu by interacting either with soluble factors or other cell surface molecules expressed on neighboring cells. The role of biochemical signals delivered by cell-cell contact versus those delivered by soluble factors interacting with cell surface receptors is not clear. The NGFR superfamily is unusual for the TNFR I and II as well as the NGFR bind to more than one ligand. The TNFRs I and II both bind to TNF-a and TNF-R. The NGFR binds to NGF, brain-derived neurotrophic factor, and neurotrophin-3.

In addition, one ligand may function as both a cell surface and soluble ligand. Recent evidence on the CD40 ligand, gp39, suggests that this ligand can exist as a membrane bound as well as a soluble ligand. It may be possible that 4-1BB is secreted and interacts with B cells in a soluble form as well as a membrane bound form. A member of the NGFR receptor family, CD27, which is expressed on T cells, is secreted in addition to being expressed on the cell surface (Hintzen et al., 1991). It is also possible that more than one 1 ligand, if soluble and on the cell surface, may bind to 4-1BB.

Isolation of the Human Homologue, H4-1BB

In order to isolate the human homologue (H4-1BB) of mouse 4-1BB two sets of polymerase chain reaction (PCR) primers were designed. To design the PCR primers, the amino acid sequence among the members of nerve growth factor receptor (NGFR) superfamily were compared because 4-1BB is a member of the superfamily (Mallett and Barclay, 1991). The amino acid sequences employed were mouse 4-1BB, human NGFR, human tumor necrosis factor receptors, human CD40, and human CD27. The areas of sequence conservation among the NGFR superfamily were chosen.

Materials and Methods

Peripheral blood lymphocytes from normal healthy individuals were isolated and activated with PMA (10 ng/ml) and ionomycin (1 mM). Messenger RNA from the lymphocytes was isolated. Using reverse transcriptase the human lymphocyte mRNA was converted to single-stranded cDNA. The cDNA was then amplified with Taq polymerase with combination of the primers (SEQ ID Nos. 3–6). A combination of primers was used and produced a specific band of about 240 bp. The 240 bp is an expected size of human 4-1BB if the human homologue protein is similar to mouse 4-1BB in size. The PCR product (240 bp) was cloned in PGEM3 vector and sequenced. One open reading frame of the PCR product was ~65% identical to mouse 4-1BB. Therefore, it was concluded that the 240-bp PCR product is the human homologue of mouse 4-1BB. The 240-bp PCR product was used to screen λgt11 cDNA library of activated human T lymphocytes. An 0.85 kb cDNA was isolated. The sequence of the cDNA is shown in SEQ ID NO:1 and the predicted amino acid sequence is shown in SEQ ID NO:2.

An expression plasmid to produce H4-1BB-AP fusion protein was constructed. The 5' portion of the H4-1BB cDNA including sequences encoding the signal sequence and the entire extracellular domain, was amplified by PCR. For correctly oriented cloning, a Hind III site on the 5' end of the forward primer and a Bgl II site on the 5' end of the reverse primer were created.

The Hind III-Bgl II H4-1BB fragment was inserted into the mammalian expression vector APtaq-1, upstream of the coding sequence for human placental alkaline phosphatase (AP).

H4-1BB-AP will be used to identify cells and tissues that express ligand for human 4-1BB (i.e. H4-1BBL). The studies with mouse 4-1BB indicated that the ligand for 4-1BB is on the cell surface. B cells and macrophages were major cells that express 4-1BBL. It is expected that H4-1BBL be expressed on human B cells and macrophages.

Results

A mammalian expression cDNA library was generated from human cell lines that express H4-1BBL. The library was screened by Iodine-labeled H4-1BB-AP. cDNA for H4-1BBL was then isolated and characterized. Soluble recombinant H4-1BBL was then produced. The generated antibodies were then used to suppress or enhance immune responses as described below. Monoclonal antibodies to H4-1BBL were produced and are discussed below.

According to studies completed by the inventor, 4-1BB acts as a co-stimulatory signal. It is expected then that H4-1BB acts as a co-stimulatory signal for T cell activation. Mouse 4-1BB helped B cells with proliferation and differentiation. H4-1BB has been found to do the same. H4-1BB-AP, H4-1BBL and various monoclonal antibodies disclosed below can be used to suppress or enhance human immune responses.

EXAMPLE 1

Production of a Monoclonal Antibody to H4-BB

The 4-1BB molecule is expressed on activated but not resting murine T cells, while cross-linking of 1 AH2 mAb directed against murine 4-1BB has been shown to enhance anti-CD3-induced T cell proliferation. Normal splenic cell antigen presentation and T cell activation can be blocked by inhibiting the binding of 4-1BB on T cells to its ligand on B cells and macrophages with 4-1BB/AP. This protein 4-1BB/AP is a fusion protein containing the extracellular domains of 4-1BB and alkaline phosphatase. Human 4-1BB mAbs were characterized, and then isolated.

Materials and Methods

Production of Recombinant Human 4-1BB

The PGEX-3 expression vector (Pharmacia) containing the full-length cDNA sequence encoding 4-1BB and the GST-binding domain of glutathionine S-transferase (GST) was constructed and the fusion protein expressed in bacteria. Fusing H4-1BB with GST, allowed for efficient purification of a recombinant H4-1BB (rH4-1BB) when isolated by GST-sepharose and a Sepharose-4B column chromatographies. The GST-binding domain is cleaved prior to immunization. The rH4-1BB fraction is purified by GST-sepharose column and Sepharose 4B column chromatographies and subsequently cleaved with factor Xa to release the H4-1BB portion prior to immunization.

BALB/c animals are immunized with a rH4-1BB protein and the spelocytes fused with the Sp2/0 fusion partner. BALB/c mice should be immunized with 50 μg of rH4-1BB emulsified in TITERMAX® (Cytrx) or Freund's complete adjuvant. Three intraperitoneal (ip) injections should be administered 2 weeks apart. Three days following the last injection, the mouse host is sacrificed and their spleens are removed. Spleen cells were fused with Sp2/0 myeloma cells. Spleen cells and Sp2/0 are mixed at 5:1 ratio and fused using 50% polyethylene glycol (PEG). Cells are then washed, re-suspended in OPTIMEM® media (Gibco), 10% fetal calf serum (FCS), 5 mM hypoxanthine, 1% aminopterin, and 0.8 mM thymidine (HAT) and cultured in 96 well U-bottom plates (Corning). Resulting cell superratants were screened by ELISA for rH4-1BB reactivity. Clones were isolated and subcloned.

Activated T cells Co-express 4-1BB+and CD45RA andCD45R0

It has been shown previously that murine 4H-1BB is associated with $p56^{lck}$ by a series of immune-precipitation studies and peptide mapping study. The data gathered indicates that 4-1BB forms a multi-peptide complex with CD45 and $p56^{lck}$ on activated T cells. To better assess the association of 4-1BB and CD45 in humans, peripheral blood mononuclear cells (PBMCs) stimulated with PHA for 48 hrs were analyzed for expression of CD45RA and CD45R0 isoforms by multi-color flow cytometry (FCM). Sixteen to 19% of cells expressed 4-1BB, and nearly all (except 1%) expressed CD45RA and nearly all express CD45R0 after correcting for non-specific binding of the antibodies.

Uses for an Anti-H4-1BB mAb

Although some mAbs specifically recognize 4-1BB expressed on SF-21 cells, they do not recognize 4-1BB expressed on activated T cells. This is likely due to the mAb having specificity for a cryptic or unique binding site(s) that is not exposed or present on T-cells but is accessible or present on SF-21 cells due to slight differences in glycosylation and processing between human T cells and insect cells (SF-21).

In mice, neither 4-1BB mRNA nor surface expression is detectable on resting splenocytes or unstimulated cloned T cells. But upon activation of T cells by anti-CD3, anti-TNF-α or anti-TNF-β, 4-1BB mRNA is detected within 3 hrs of stimulation and is first detectable on the cell surface 2–3 days following stimulation. Maximum surface expression is reached about 6 days following stimulation. As in the mouse, 4-1BB is not detected on the surface of freshly isolated peripheral blood T cells in man, but is readily detected following PHA stimulation. Unlike in the mouse, 4-1BB is expressed much more rapidly in humans, reaching a peak expression level within 12–48 hrs. 4-1BB expression begins to decrease within 72 hrs., post-stimulation, as do the number of cells expressing 4-1BB on their cell surface. In both mouse and humans, 4-1BB is expressed on CD4+ and CD8+ T cell subsets.

4-1BB is associated with $p56^{lck}$. A 56 kDa protein is detected when $[^{32}P]O_4$ was transferred from gamma-labeled adenosine triprìosphate (ATP) onto the p56 protein in ConA activated thymocytes that were subjected to immunoprecipitation with anti-4-1BB mAb, 1AH2. By peptide mapping, this 56 kDa phosphoprotein was identified as $p56^{lck}$. The $p56^{lck}$ and 4-1BB molecules were also found to be co-immunoprecipitated in insect cell studies (SF-21) and in HeLa cells transfected with 4-1BB and $p56^{lck}$. Furthermore, cross-linking of 4-1BB activated $p56^{lck}$. Cysteine residues critical for $p56^{lck}$-CD4/CD8 complex formation were also critical for $p56^{lck}$-4-1BB interaction. In preliminary results, it was noted that anti-4-1BB also immunoprecipitated a protein of ~200 kDa from biotin-surface labeled ConA activated thymocytes. When anti-CD45 mAb was used br immunoprecipitation, a ~30 kDa protein, of similar size to murine 4-1BB, was detected. Others have previously shown that CD45 mediates the dephosphorylation of certain proteins such as $p56^{lck}$ (Biffen et al., 1994). Perhaps 4-1BB plays a role in bringing CD45 and $p56^{lck}$ together and facilitates the dephosphorylation of $p56^{lck}$ by the CD45 phosphatase.

To further assess the association of 4-1BB and CD45, PHA-stimulated PBMCs were analyzed by multicolor FCM. Approximately 16–19% of PBMCs cultured in PHA for 48 hrs express 4-1BB. If all 4-1BB+ cells express CD45RA and express CD45R0, the ~17.5% of 4-1BB+ cells must co-express both CD45RA and CD45R0 on their cell surface. Of the PHA-stimulated $CD45RA^{hi}R0^{hi}$ cells, approximately 50% express 4-1BB. This data further supports the hypothesis that CD45 and 4-1BB share an association. More importantly, it suggests that 4-1BB may play a role in T cell transition from a naive phenotype ($CD45RA^{hi}R0^{lo}$) to a memory phenotype ($CD45RA^{lo}R0^{hi}$). Picker et al. previously demonstrated through multi-color FCM, that naive T cells undergo a "stepwise, unidirectional progression" from a naive ($CD45RA^{lo}R0^{hi}$) to a memory ($CD45RA^{lo}R0^{hi}$) phenotype through a distinct $CD45RA^{hi}R0^{hi}$ intermediate cell type. Few peripheral blood cells that express this intermediate phenotype are detectable. However, in secondary lymphoid tissue, such as tonsil, 2–10% of T cells were found to be $CD45RA^{hi}R0^{hi}$. Much is known about the naive and memory T cells, but little is known about the $CD45RA^{hi}R0^{hi}$ in transitional cells. Nor is it known what events occur during this transition phase that result in memory T cell development. Therefore, it will be necessary to assess the role of 4-1BB in the transition from a naive to that of a memory T cell and the apparent association of 4-1BB and CD45. In this regard, anti-H4-1BB mAb's are invaluable.

Results

The anti-H4-1BB mAb can be used to enhance T-cell cross-linking and therefore induce T-cell activation against certain types of cancer cells (e.g. melanoma). By using the mAb in experiments with various cancer cells in the presence of T-cells dosages and proper formulations of initiating T-cell activation against the cancer cells can be determined. The formulations are tested in animal models with the same type of cancer and the formulations and dosages are refined for testing in humans.

Sinovial T-lymphocytes in patients with rheumatoid arthritis express H4-1BB, but 4-1BB is not expressed in sinovial T-lymphocytes of patients without this disease. This disease involves an undesired immune response against the patient's own tissue. Therefore, blocking the undesired immune response would provide relief for the arthritis sufferer. By injecting the patient with an anti-H4-1BB mAb or the fusion protein, the binding between H4-1BB and its ligand would be blocked. If the binding of an mAb and H4-1BB did not enhance activation of the immune system, then the anti-H4-1BB mAb interference with binding would have the desired effect, otherwise the fusion protein would be used for blocking binding. The fusion protein (monomeric) should not stimulate H4-1BB or its ligand but is a good ligand binding blocker because it binds to the H4-1BB ligand thereby preventing H4-1BB from binding and stimulating the ligand.

A similar method of blocking ligand binding would be useful for treating patients with systemic lupus erythematosus. For patients with Type I diabetes—T-cells attack their own insulin producing cells, pancreatic Beta cells. By injecting the mAb or fusion protein this destruction can be blocked.

Peripheral blood T cells in patients with AIDS or certain types of viral flu are expressing H4-1BB, whereas the same cells in normal patients are not expressing H4-1BB. Therefore, 4-1BB is important in this immune response. The enhancement or blocking of H4-1BB ligand binding or cross-linking will be important in regulating the T-cells in patients with these diseases.

EXAMPLE 2

Uses of H4-1BB Antibodies in the Suppression of Immune Responses

FIGS. 1 and 2 illustrate the molecules involved in T-cell-activation. During early T-cell activation (cognitive phase), resting T cells express the TCR/CD3 complex and other "accessory" molecules. Among these constitutively expressed molecules, CD4+ (or CD8+), LFA-1, and CD28 are probably the ones to receive co-stimulatory signals. Initial interaction with the TCR/CD3 complex in combination with these 'accessory' co-stimulatory signals leads to subsequent expression of additional receptor molecules such as CD28, CTLA4, and 4-1BB. These newly expressed molecules will receive additional important co-stimulatory signals at later stages of T-cell activation, such as during clonal expansion.

Figure 4:
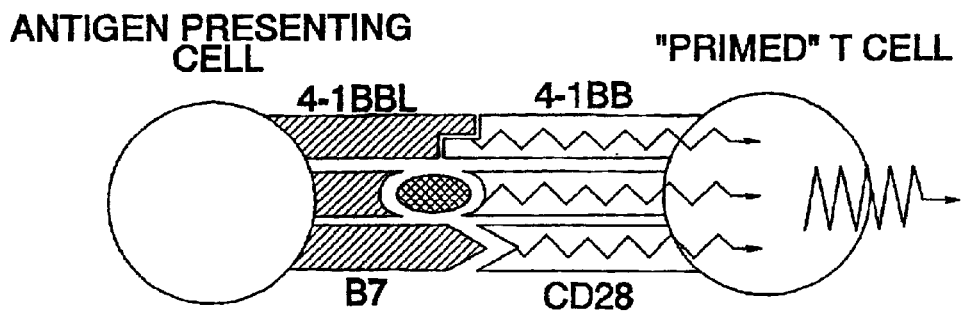
FIG. 4 illustrates a "primed" T-cell during the normal T-cell activation pathway.
Figure 5:
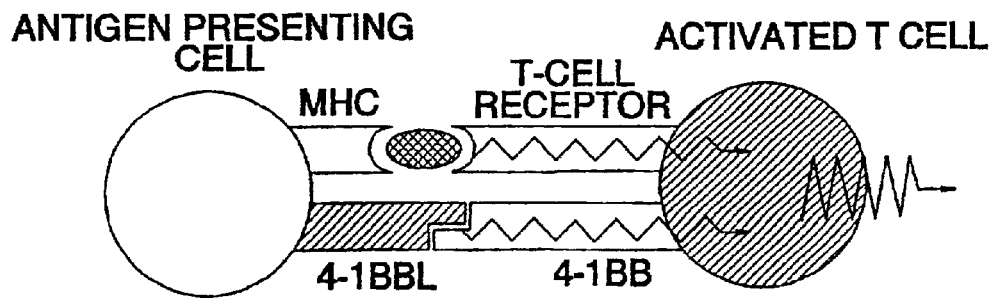
FIG. 5 illustrates an activated T-cell which was activated through the presence of a non-self, antigen presenting cell, representing the conclusion of the normal T-cell activation pathway.
Figure 6:
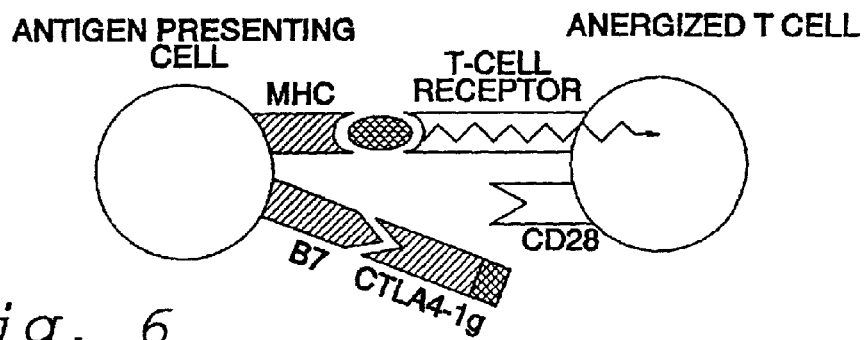
FIG. 6 illustrates a anergized T-cell CTLA4-lg alone, 4-1BB/AP and CTLA4-lg together and 4-1BB/AP alone respectively being used to block steps in the T-cell activation pathway.
Figure 7:
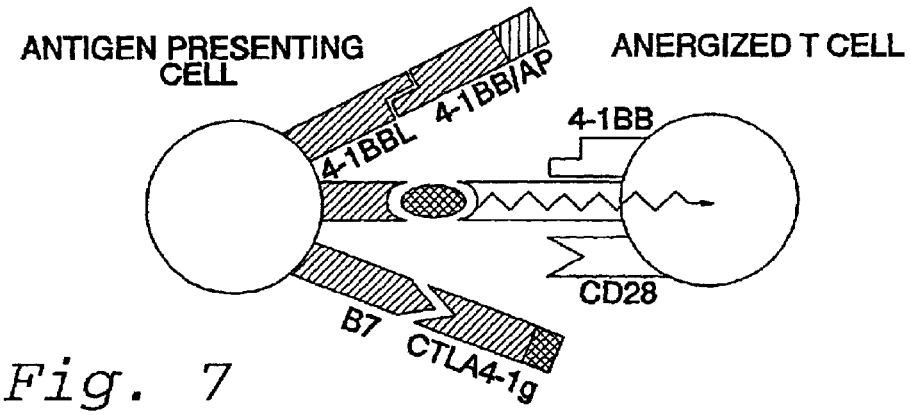
FIG. 7 illustrates 4-1BB/AP and CTLA4-lg together in an effort to block the T-cell activation pathway.
Figure 8:
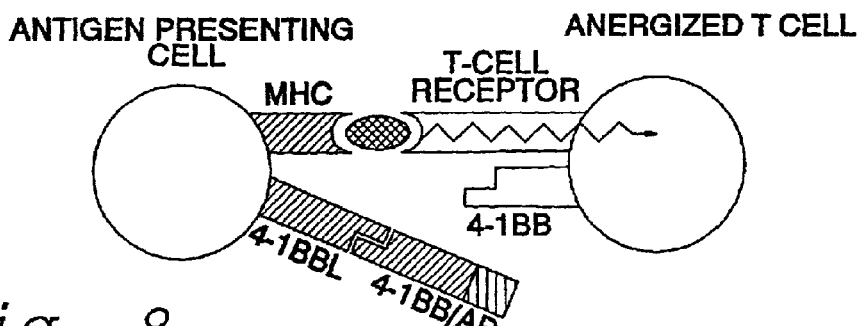
FIG. 8 illustrates 4-1BB/AP alone where it is used to block steps in the T-cell activation pathway.

FIGS. 3–5 illustrate a normal T-cell activation pathway. FIGS. 6–8 illustrate the blocking of immune responses with soluble chimera of 4-1BB. If 4-1BB plays a role in T-cell activation, blocking of the interaction to its ligand on antigen-presenting cells will result in suppression of T-cell dependent immune responses. It is well documented that blocking of the interaction of CD28 to its counter-receptor B7 suppresses in varying degrees, both in vivo antibody production and cell-mediated immune responses. Blocking of both interactions should result in a more effective immunosuppression; since 4-1BB is induced during T-cell activation. Blocking of the interaction of 4-1BB to its ligand is of importance at later stages of the activation process where the CD28/B7 interaction is no longer be of relevance.

As illustrated with mouse receptor 4-1BB and mouse ligand 4-1BBL above, addition of H4-1BB-AP will coat the H4-1BBL expressing cells and block the normal interaction between H4-1BB and H4-1BBL. This will lead to immunosuppression. This type of immunosuppression is antigen-specific. Therefore, it avoids the generalized immunosuppression produced by anti-CD3 or cyclosporin A treatments. H4-1BB-AP treatment can be used to treat certain autoimmune diseases and to facilitate organ transplantation.

Binding Activity

The portion of the receptor protein H4-1BB binds to the cell membrane ligands and binding can be detected by relative activity assays for the detection protein. The fusion protein is placed in the presence of a cell suspected to express the receptor protein H4-1BB. Then the cell is washed of any fusion protein not bound to the cell membrane ligands. Once the washed cells are placed in the presence of a substrate for the detection protein and the relative activity of the detection protein can be measured.

Enhancement of Immune Reaction

H4-1BB may function at the late stage of T cell activation and may be a critical molecule for completion of T cell activation. Most tumors display tumor-specific antigens. One reason, however, why immunogenic tumors can escape host immunity is that tumor-reactive T cells receive inadequate co-stimulation. The introduction of the co-stimulatory molecules, such as H4-1BB into the tumor, therefore, could enhance the antitumor immunity of cytotoxic T cells (CTL) by upregulating activity. H4-1BBL can be expressed in cell-specific fashion. For example, the H4-1BBL can be expressed in melanoma using melanocyte-specific promoter such as tyrosinase promoters. The H4-1BBL-expressing melanoma will stimulate cytotoxic T cells through H4-1BB and activate the melanoma-specific CTL. The activated melanoma-specific CTL can then destroy the target cancer (e.g. melanoma).

EXAMPLE 3

Co-Stimulation of CD28 with Human 4-1BB to Promote Type 1 Cytokines

An investigation was made to determine the role of H4-1BB in CD28 stimulation. Also studied was whether CD28 requires an additional co-stimulatory signal to promote human effector T cell development. In that effort it was known that the cytokine IL-2 cooperates with CD28 in inducing IF production in Th1 cells. in vitro, it was determined that IL-2 is not an absolute requirement for antigen-induced priming of a Th1 response, although its presence during priming enhances the ability of antigen-primed Th1 cells to produce IF (gamma interferon). IF produced by Th1 cells amplifies Th1 development and inhibits proliferation at Th2 cells, whereas IL-4 produced by Th2 cells blocks development of Th1 cells. Once a T cell immune response begins to develop to Th1 or Th2, it tends to become progressively polarized in that direction. It remains unclear whether initial cytokine secretion of T cells is determined by an independent regulatory process.

T cell activation requires a signal delivered through TCR and a second signal, mostly through CD28, referred to as co-stimulation. T cells activated in vitro in the absence of a CD28 signal are defective in their response to forthcoming antigenic stimulus and are characterized as anergetic (e.g. "anergized"). When human T cells were repeatedly reactivated in vitro with anti-CD28, the process reduced IL-2 production, and induced IL-4 to produce Th2-like cells. Studies of response to antigen specific cytokine production in CD28-deficient mice demonstrated that IL-4 and, to a lesser extent, IF production are augmented by CD28-mediated signals.

CD28 signaling has recently been shown to prevent apoptosis, a phenomenon known as activation-induced cell death (AICD) both in anti-CD3-activated murine and human T cells. Repeated TCR engagement results in an accumulation of cells that express Fas or a prolonged unresponsiveness to CD28 signaling. The loss of CD28 responsiveness and acquisition of Fas might result normally after prolonged stimulation, providing a mechanism to prevent the reactivation of effector T cell populations. Therefore, co-engagement of additional co-stimulatory factors to CD28 should be required to protect the cells from AICD for long-term T cell maintenance and effector T cell differentiation.

The CD30 molecule is preferentially expressed by human CD4+ and CD8+ clones with Th2-type cytokine profile. There is an inverse correlation between CD30 expression and production of IF. The expression of 4-1BB and CD30 is equally activation-dependent and is confined predominantly to CD45R0+ cells. Exposure to 4-1BB supported IL-2 production and proliferation of murine splenic T cells. The 4-1BB molecule is expressed both on CD4+ and CD8+ T cells and is associated with $p56^{lck}$.

It is disclosed herein that 4-1BB plays regulatory roles with CD28-mediated co-stimulation to specifically promote type 1 cell development, as well as to prevent AICD. 4-1BB-mediated type 1 responses were not observed in CD30-positive cells. The current results indicate that 4-1BB and CD30, whose expressions are mutually exclusive, may counteract to regulate the balance of types 1 and type 2 development.

Materials and Methods

Antibodies and Reagents

Monoclonal anti-4-1BB, was used to ligate 4-1BB and stain 4-1BB on T cells for flow cytometric analysis. Anti-CD28, mAb 9.3 (mouse IgG2) was a kind gift from Dr. Carl H. June, and CD28.2 (mouse IgG$_1$) was purchased from PharMingen (San Diego, Calif.). Monoclonal antibody to human CD3 (OKT3, mouse IgG$_1$) was purchased from Ortho Diagnostic (Westwood, Mass.). Secondary cross-linking goat anti-mouse IgG (H+L), and anti-mouse $IgG_1$-fluorescein isothiocyaflate (FITC) for flow cytometry were purchased from Zymed (South San Francisco, Calif.) and Southern Biotechnology Associates (Birmingham, Ala.), respectively. Anti-IF-Phycoerythrin (PE), anti-IL-4-PE, anti-CD4-Cy-Chrome, and PE labeled mouse $IgG_1$ isotype control (MOPC-21) were purchased from PharMingen. 4-1BBFc, a fusion protein consisting of the extracellular portion of human 4-1BB coupled with Fc region of human IgG (38), was obtained from Immunex (Seattle, Wash.). An isotype control mouse IgG, was purchased from Sigma (St. Louis, Mo.). A premixed cocktail of monoclonal antibodies, and complement (LymphoKwik) to isolate T helper cells was purchased from One Lambda (Canoga Park, Calif.).

Cells

Human PBMC were isolated from buffy coats of healthy donors by Histopaque-1077 (Sigma) density centrifugation. CD4+ T cells were purified from PBMC by depleting CD8+ T cells, B, and macrophage cells by the corresponding monoclonal antibodies and complement. The purity of CD4+ T cells was about 85%, as determined by flow cytometric analysis. The purified T cells or PBMC at $1 \times 10^6$ cells/ml were activated by phytohemagglutinin (PHA, Calbiochem) at 5 µg/ml for 4 days and, after washing to remove PHA, were subsequently expanded in the presence of IL-2 at 100 µl/ml from 3 to 10 days depending on the following experiments with replacement of fresh IL-2 every 3 days. The resulting cells with >95% T cells are hereinafter referred to as "PHA/IL-2 cells." For the proliferation assays, cells were cultured for 10 days in IL-2 until all the clustered PHA blasts became completely dispersed, with reduced cell sizes before reactivation.

Reactivation of T Cells

The PHA/IL-2 cells from purified CD4+ T cells or PBMC were reactivated with 1 µg/ml soluble anti-CD3 mAb in the presence of 5-fold excess goat anti-mouse IgG in the plates (Costar, Cambridge, Mass.) coated with isotype control mouse $IgG_1$, (MOPC-21), or antibodies to CD28 in the presence of additional antibodies to 4-1BB, CD30 or a combination of the two antibodies, 10 µg/ml each at 4° C. overnight. After 3- to 5-day anti-CD3 activation, the cells were transferred to new plates coated with antibodies in the same way to repeat another cycle of reactivation, if necessary.

Cytokine Production

Following anti-CD3 reactivation of PHA/L-2 cells in 24-well plates coated with an isotype control mouse $IgG_1$, anti-4-1BB, anti-CD28, and a combination of anti-4-1BB and anti-CD28 at 10 µg/ml each antibody, conditioned media were collected in order to measure IL-2, IF, TNF-α, IL-4, and TGF-β. The cytokine IL-2 was assayed by an IL-2-dependent cell line, CTLL-2 and the rest of cytokines were measured by commercially available ELISA kits; IF (Endogen), TNF-α (Genzyme), IL-4 and TGF-β (R and D Systems).

Cell Proliferation Assay

The primary T cells were repeatedly activated by three consecutive cycles as described above. After each three cycles of anti-CD3 activation, cells were collected and reactivated by antiCD3, 1 µg/ml and cross-linking anti-mouse IgG, 5 µg/ml to measure the responsiveness to the immobilized anti-CD28 or anti-4-1BB or both antibodies in anti-CD3-mediated TCR activation in 96-well microtiter plates ($5 \times 10^4$ cells/200 ul/well). Anti-CD28 at designated concentrations with or without additional anti-4-1BB (10 µg/ml) was coated onto 96-well plates in PBS at 4° C. overnight. Incorporation of [$^3$H] thymidine was measured for the last 6 hours of the 3-day culture.

Flow Cytometry

For measuring 4-1BB expression, approximately $2 \times 10^6$ cells reactivated in the different co-stimulatory conditions were washed, suspended in a 100 µl of 2 µg/ml anti-4-1BB in staining solution (PBS containing 1% BSA), and incubated at 4° C. for 30 minutes. The cells were subsequently washed three times, re-suspended in 200 µl of FITC-conjugated anti-mouse $IgG_1$, 1 µl/ml, and incubated for 30 minutes. After being washed, the samples were fixed with 1% paraformaldehyde prior to flow cytometric analysis on the FACScan (Becton Dickinson, Mountainview, Calif.). Gates were set on live cells only, based on forward-versus-side scatter profiles. In every case at least 10,000 events were collected for each sample. For measuring intracellular IF and IL-4 levels, the protocols recommended by the manufacturer were followed (incorporated herein by reference).

PBMC activated with PHA were repeatedly activated for 3 days by anti-CD3 and anti-CD28 with or without anti-4-1BB, collected, washed, and stained for surface 4-1BB, and CD30 with anti-4-1BB-FITC and anti-CD30-FITC, respectively as described above. To identify 4-1BB and CD30, two-color staining with anti-4-1BB-biotin and streptavidin-PE for 4-1BB and anti-CD30-FITC for CD30 was used. Following the fixing of the cells with 4% parafonnaldehyde and permeabilization with 0.1% saponin, the cells were further stained with IF-PE or IL-4-PE at 1 µg/ml, in 0.1% saponin. Cells were finally re-suspended in PBS containing 1% BSA and analyzed for two-color stained surface markers and intracellular cytokines by fluorescence-activated cell sorter (FAGS) scan. In some cases, the cells were stained for CD4 in addition to 4-1BB or CD30 with anti-CD4-Cy-Chrome before intracellular staining.

Results

The maximal expression of 4-1BB was seen after repeated activation by its own signal (e.g., positive feedback loop). CD28 is expressed on the majority of naive and memory T cells. In contrast to CD28, 4-1BB, another co-stimulatory molecule, were not detected in naive T cells freshly prepared from healthy volunteers. The activation conditions for the maximum 4-1BB expression on human T cells were also investigated. Expression of 4-1BB was induced by PHA or anti-CD3 stimulation with maximum plateau levels after 3 to 4 days. At peak, less than 20% of T cells were 4-1BB-positive.

Upon resting in IL-2 (100 u/ml) for 10 days, following PHA stimulation (referred to as PHA/IL-2 cells), 4-1BB expression declined to less than 5% of T cells positive. Reactivation of PHA/IL-2 cells by anti-CD3 and anti-CD28 in the presence or absence of anti-4-1BB gave rise to a remarkable increase of 4-1BB. More than 50% of T cells became 4-1BB-positive in 3 days. The high 4-1BB expression was transient, and continuous anti-CD3 reactivation with anti-CD28 alone for the next cycle of reactivation did not maintain 4-1BB expression resulting in less than 10% 4-1BB positive cells. In contrast, 4-1BB co-engagement with anti-CD28 co-stimulation resulted in a dramatic difference, leading to a continuous increase in 4-1BB expression to higher than 60% with repeated activation. This finding indicates that high 4-1BB expression requires repeated TCR activation with co-stimulatory signals from both CD28 and 4-1BB. Anti-CD3 activation with 4-1BB co-stimulation without CD28 involvement resulted in only modest effects on the 4-1BB induction.

It was therefore determined that the 4-1BB signal plays an important role in its own expression, with CD28 remaining essential. The high 4-1BB expression caused by co-stimulation of its own signal with CD28 may provide the means for polarizing to 4-1BB-expressing T cells through positive feedback loops during repeated antigen challenge in vivo. The 4-1BB signal regulated CD28 co-stimulation to enhance type 1 cytokine but to suppress type 2 cytokine production.

PHA/IL-2 cells were reactivated by anti-CD3 with co-stimulatory antibodies to 4-1BB, or CD28, or a combination of both 4-1BB and CD28. The cytokines secreted into the conditioned media following 3-day-reactivation were assayed. Since 4-1BB is induced both in CD4+ and CD8+ cells. The designation given the effector phenotypes for CD4+ and CD8+ T cells was collectively type 1 and type 2, respectively, instead of Th1 or Th2. The 4-1BB signal enhanced IL-2, TNF-α, and IF, which are largely classified as type 1 cytokines, several times higher than the levels induced by CD28 co-stimulation alone. Among the induced cytokines, IF (gamma interferon) was most significantly enhanced by 4-1BB (7.3-fold). The 4-1BB alone, without CD28 co-stimulation, did not show significant effect. It was surprising that additional 4-1BB signal to CD28 instead suppressed IL-4, a type 2 cytokine and TGF-β, to a lesser degree, below the levels induced by CD28 co-stimulation alone. The 4-1BB signal suppressed CD28-mediated IL-4 production in a dose-dependent manner. These results indicate that 4-1BB plays a regulatory role in inducing specifically type 1 and suppressing type 2 cytokine production as well when co-engaged with CD28 co-stimulation.

The 4-1BB signal expanded IF-producing cell population exclusively in CD30-negative cells. Concurrent enhancement of type 1 and suppression of type 2 cytokine production by 4-1BB signaling spurred the examination as to whether 4-1BB co-engagement with CD28 in co-stimulation was actually involved in the induction of type 1 subset T cell development. The IF-producing cells were identified at the single-cell level by detecting intracellular IF by flow cytometry.

PHA/IL-2 cells produced IF-producing cells in 3% of the total population upon reactivation with anti-CD3 and anti-CD28. The same cells reactivated by anti-CD3 and anti-CD28 with additional anti-4-IBB, increased IF-producing cells to more than 15% of the population. Therefore, enhanced IF in the culture medium as a result of 4-1BB co-engagement to CD28 in co-stimulation may be attributed to an increase of IF-producing cells. It is not known whether IF-producing cells were developed directly by the 4-1BB signal or indirectly by the promoted cytokines or a combination of both.

The IF-producing cells generated by anti-4-IBB were further identified by two surface markers, 4-1BB and CD30, another inducible co-stimulatory molecule with structural homology to 4-1BB as members of TNF receptor superfamily. Other investigators have proposed CD30 as a potential Th2 marker. The majority of IF-producing cells were 4-1BB-positive. Conversely to 4-1BB, the same IF-producing cells appeared to be predominantly CD30 negative. These results indicate that the 4-1BB signal is involved in expanding specifically IF-producing but CD30- negative cells possibly due to type 1 subset-specific 4-1BB expression. A positive correlation between the intensities of intracellular IF and surface 4-1BB expression, as manifested in the dot plot by tilted cone-shaped patterns was also found. The positive correlation of IF and 4-1BB expression supports the view that the 4-1BB signal is directly involved in de novo IF induction, as well as expansion of IF-producing cells. The 4-1BB protein was expressed preferentially on IF-producing, not on IL-4-producing T cells Because 4-1BB-induced IF-producing cells lacked CD30, next examined was whether 4-1BB expression was exclusively limited to the cells with type 1 phenotype. For the purposes of this disclosure gamma interferon and IL-4 cytokines were chosen as representative marker cytokines for types 1 and 2 phenotypes, respectively, and compared the level of 4-1BB expression in two subset populations.

The PHA/IL-2 cells were reactivated by anti-CD3 with anti-CD28 and anti-4-1BB for 3 days, and were stained for surface 4-1BB and, subsequently identified by marker cytokines, IF or IL-4. The level of 4-1BB expression in the populations gated out for IF- and IL-4-positive cells were compared. A significant difference in 4-1BB expression levels between the IF and IL-4-producing cells was found. The 4-1BB expression was highly enriched in IF-positive cells (61.7%) compared to IL-4-producing cells (22.7%). These results indicate that 4-1BB is not randomly, but preferentially expressed on type 1 subset cells. 4-1BB and CD30 are mutually exclusive in expression.

The results indicate that 4-1BB mediates type 1 T cell differentiation based on the preferential 4-1BB expression on the IF-producing cells and its ability in inducing IF production. On the other hand, other groups have demonstrated that CD30 is a Th2 marker or a marker for the IL-4 response. Also examined was whether 4-1BB and CD30 expression were exclusively divided into two different subsets of T cell populations. The surface expression of 4-1BB and CD30 by flow cytometry in CD4+ T cells using two-color staining was analyzed. Both 4-1BB and CD30 were expressed on CD4+ and CD4− cells that were more than 95% CD8+. The correlation of 4-1BB and CD30 expression in CD8+ cells was analyzed because 4-1BB expressed predominantly on CD8+ cells. 4-1BB and CD30-expressing cells were largely divided into two separate groups with only a minor cell population shared with both 4-1BB and CD30. These CD4+ cells also gave rise to similar 4-1BB and CD30 expression patterns with mutually exclusive expression with one another. The results demonstrated that 4-1BB and CD30 were mutually exclusive in expression on T cells, and this mutual exclusiveness of the two molecules did not result from their differential dominance in expression between CD4+ and CD8+ cells.

4-1BB Signaling Down-Regulated CD30-positive Cell Population

Considering that both 4-1BB and CD30 are co-stimulatory molecules, the possibility of cross-regulation between 4-1BB and CD30 in developing CD30-producing cell populations was examined. To do this the levels of CD30-expressing cell development were measured by flow cytometry during early activation in response to 4-1BB and CD30 signaling. PHA-activated (2 days) PBMC were immediately reactivated for 2 days with anti-CD3 and anti-CD28 plus additional antibodies to 4-1BB or CD30, or both 4-1BB and CD30. It was determined that the 4-1BB and CD30 signaling counteracted one another in the levels of CD30-producing cell development. 4-1BB signaling clearly down-regulated the CD30 levels below the levels of the cells reactivated with CD28 alone. CD30 signaling increased CD30-positive cell population in exactly the same manner that 4-1BB-induced 4-1BB expression. The 4-1BB signal reversed the effect of CD30 when both 4-1BB and CD30 signals were present. 4-1BB and CD30 signaling might cross-regulate each other's functions, by down-regulating the cell population with counterpart molecules through the release of antagonistic cytokines, for example, IF and IL-4. The results support that 4-1BB and CD30 may be primarily responsible for the maintenance of the subset cells in expressing their own molecules. Regulation in co-engagement of 4-1BB and CD30 with CD28 during repeated TCR activation may provide another controlling mechanism for polarizing type 1 and 2 development. Co-engagement of 4-1BB signal with CD28 co-stimulation was critical to maintain proliferation during repeated anti-CD3 activation It was also discovered that after multiple cycles of reactivation of previously activated cells by a high dose of soluble anti-CD3, significant cell death was seen. This was true even in the presence of substantial amounts of anti-CD28. These results are consistent with recent reports by others that TCR reengagement induced apoptosis after a strong initial proliferative response to antigen, and large concentrations of IL-2 for cell cycle progression. One of the consequences of repeated in vitro activation, especially following an exposure to high dose IL-2, is the gradual loss of responsiveness to CD28 co-stimulation. The repeated TCR activation, a condition for cell death, instead, induced 4-1BB expression. It is therefore believed that continuous reactivation may cause irreversible damage, leading to apotosis, even in the presence of CD28 signaling, and that co-engagement of 4-1BB with CD28 could prevent the anti-CD3 reactivation driven apoptosis. The effects of 4-1BB on cell proliferative activity during in vitro repeated activity by anti-CD3 and anti-CD28 was studied. The PHA-activated T cells, after IL-2 stimulation for 10 days until the T cell blasts returned to smaller cell sizes, were continuously reactivated by anti-CD3 and anti-CD28 with or without 4-1BB co-engagement. After each of three cycles of reactivation, the cells were reactivated again by anti-CD3 in 96-well plates coated with serially diluted anti-CD28 from 0.01 to 10 μg/ml with or without an additional 10 μg/ml of anti-4-1BB.

The cells were examined for proliferative activity by measuring [$^3$H]thymidine incorporation. As the number of reactivation cycles proceeded, cells became less responsive to anti-CD28, resulting in a lower maximum proliferation plateau, even with saturated anti-CD28 concentrations. After the third cycle re-activation, T cells barely responded to anti-CD28 alone. The 4-1BB co-engagement with CD28, however, exerted a dramatic effect in overcoming the defective proliferation, as well as fully restoring maximal plateaus of expression. The 4-1BB signal alone failed to demonstrate a strong level of expression. The 4-1BB effects were blocked by the functional antagonist, 4-1BBFc, the soluble form of 4-1BB when it was included in reactivation, indicating the specificity of anti-4-IBB.

Because the most significant 4-1BB effects were observed after the response of anti-CD28 has been weakened by anti-CD28 repeated activation, one of the primary functions of 4-1BB response, is likely to maintain clonal expansion by synergistic cooperation with CD28 during continuous high-dose antigen re-challenge.

Effects of the 4-1BB on Progression of the Cell Cycle in Repeatedly Activated T cells Since both cell proliferation and death events occurred simultaneously during repeated in vitro CD-3 activation, the effects of 4-1BB signal on cell cycle progression and apoptotic events was determined. This was accomplished by measuring DNA stained with propidium iodide. Staining was done during reactivation.

In order to examine the effect of 4-1BB signal transduction on cell cycle and apoptotic status during AICD, the PHA/IL-2 cells were reactivated with anti-CD3, anti-CD28, or anti-4-1BB alone, or with a combination of both antibodies for 3 days in two cycles. The DNA content of cells stained with propidium iodide were analyzed by the ModFit software program.

Consistent with previous proliferation results, neither anti-CD28 nor anti-4-1BB ligation alone gave rise to a significant cell population in S-phase (less than 10%), but a relatively high fraction was in sub-G-phase supposedly representing apoptotic cells. Simultaneous ligation of 4-1BB and CD28 resulted in a dramatic increase of the cell population in the S phase (higher than 40%), and a concomitant decrease in sub-G-phase cells. These results indicate that additional co-stimulation between 4-1BB and CD28 was essential, not only for enhancing the progression of cells through the G1/S phase transition, but also for preventing apoptotic cell death during chronic stimulation. The 4-1BB molecule is a regulatory co-stimulatory molecule for promoting type 1 subset development in cooperation with CD28.

The data disclosed herein support a two-step model of activation of T cells. In the first step, T cell activation involves CD28-B7 recognition as a co-stimulatory signal with antigenic signal via TCR. As a result of primary T cell activation, the activated T cells can enter into secondary cognate dependent recognition. The new regulatory co-stimulatory molecules and their ligands, provided by activated APCs, will interact by sequential cross-talk between T cells and APCs in a way specific for the different circumstances. In the secondary activation phase, cells will require additional signals besides CD28-B7 recognition in order to prevent TCR activation-driven cell death, as well as to promote effector cell differentiation, especially after cells progress through many cycles of division. In this model, the cognate-dependent recognition of new regulatory molecules must be tightly regulated to deliver either the survival or death signal.

To delineate the role of 4-1BB, an experimental model with in vitro repeatedly activated cells was adopted. CD28 alone appeared to be incapable of maintaining cell cycling after cells were repeatedly activated. The results indicate that the co-engagement of 4-1BB and CD28 maintained long-term proliferative activity. Therefore, 4-1BB may be able to inhibit complex regulatory networks by CD30 or Fas which promotes cell death. In this context, 4-1BB is a survival factor specifically directed to type 1 cells in the secondary activation phase. Moreover, it has been shown that 4-1BB co-engagement with CD28 is critical to the promotion of type 1 phenotype responses, and in the specific expansion of the cell populations expressing 4-1BB.

Delayed type hypersensitivity (DTH) is mediated primarily by cells of the T cell subpopulation Th1 that produce IF. Alteration of the T cell subpopulation Th1/T cell subpopulation Th2 (Th1/Th2) regulatory networks may be important in determining the local immune responses. The production of Th2 cells provides a strong foundation for their anti-inflammatory effects in vivo. Recently, it has been reported that the CD28/B7 pathway selectively promotes Th2 development for autoantigen-specific T cells in the non-obese diabetic mouse. Blockade of 4-1BB-mediated Th1 responses to induce anti-autoimmune Th2 cells is thus a good approach for antigen-specific therapies for the harmful DTH reaction involved in autoimmune diseases. The pathogenic progression of HIV infection also has been associated with diminished type 1 and enhanced type 2 cytokine production. Therefore, enhancing the activity of type 1 cytokines would have the benefit of offering a way to intervene in HIV-infected individuals. CD30 signal enhances both HIV transcription and IL-4 production, in response to CD3 antibody. Therefore, continuous use of anti-CD28 co-stimulation would prevent or hinder HIV-1 promotion.

EXAMPLE 4

Use of Anti-H4-1BB Antibodies Against HIV-1 Infected Cells 4-1BB is not detected in human peripheral blood T lymphocytes, but it is induced by stimulation with mitogen and/or cross-linking of CD3, ranging from 5% to 20%, followed by a gradual decrease after prolonged activation. Signaling through 4-1BB is involved in the regulation of proliferation and survival of T lymphocytes. 4-1BBFc fusion protein prevented anti-CD3-induced proliferation and caused cell death, not only in murine splenocytes, but also in human PBMC. Recently, it was determined that the CD28 molecule co-stimulation was essential for the induction of 4-1BB, which in turn enhanced its own expression as a positive feedback loop upon continuous stimulation. The 4-1BB signal resulting from combined co-stimulation from both CD28 and 4-1BB subsequently facilitated cell survival and effector cell development. In HIV-1 infection, CD28 expression is down-regulated, as manifested by a significant correlation observed between the number of CD28 and CD8+ T cells and the presence of HIV-1-related disease. Previous studies by others indicated that co-stimulation of CD4+ T cell via soluble monoclonal antibodies against CD28 promoted HIV-1 infection and replication in vitro. In contrast to these results, when CD4+ T cells from HIV-1 individuals were stimulated with immobilized anti-CD3 plus immobilized anti-CD28 mAb, there was an increased number of polyclonal CD4+ T cells with a declined HIV-1 viral load.

The Role of 4-1BB in T Lymphocytes from HIV-1 Infected Individuals

The levels of 4-1BB expression on T cells from 40 HIV-1 positive and 12 HIV-1 negative individuals were compared. Also examined was whether T cells from HIV-1 positive individuals, impaired in their response to TCR/CD3-mediated signal, could be restored by 4-1BB co-stimulation, and the effects of 4-1BB ligation on HIV-1 viral load.

Materials and Methods

Patients

The HIV-1 infected patients' blood samples were from the outpatient clinic at Wishard Hospital Department of Medicine, Division of Infectious Diseases. The study covered 55 HIV-1 positive individuals, of which 47 were classified as CD stageII/III and 18 were classified as having HIV-1 related diseases (stage IV). Twelve sex- and age-comparable healthy donors were studied as controls.

Antibodies and Reagents

The anti-4-IBB monoclonal antibodies (mAbs), BBK-1, BBK-2, BBK-3 and BBK-4 were produced as described previously. BBK-1 and BBK-4 are agonistic for T cell activation and were used in the present studies. BBK-2 and BBK-3 are H4-1BB antagonists, and were also developed and used for the present studies. FITC-conjugated anti-4-IBB mAb and was generated by incubating the purified BBK-1 with FITC (Pierce, Rockford, EL) according to the manufacturer's instructions. Anti-CD28 mAb, 9.3, was a gift from Dr. Carl June (Naval Medical Research Institute, Bethesda, Md.). Anti-CD3 mAb was purchased from Ortho Raritan, N.J.). Anti-CD4 mAb/Cychrome, anti-CD8 mAb/Cychrome and isotype control mAbs were obtained from Pharmingen (San Diego, Calif.). Magnetic beads that were conjugated with Goat anti-mouse IgG (M-450) were purchased from Dynal (Lake Success, N.J.).

Cells and Cell Stimulation

Human peripheral blood mononuclear cells (PBMC's) were prepared from EDTA anti-coagulated blood by Histopaque 1077 (Sigma, St. Louis, Mo.) density centrifugation. CD4+ T cells were prepared from PBMC by negative depletion using Lymphokwik (One Lambda Inc., Canoga Park, Calif.) according to manufacturer's instruction. Briefly, PBMC were treated with Lymphokwik Th isolation solution for 45 min at 37° C. followed by a 5 minute centrifugation. The purity of CD4+ T cells were around 85–90% with less than 5% CD8+ T cells by flow-cytometric analysis. The culture medium was RPMI 1640 (Life Technologies, Inc.) supplemented with 10% fetal bovine serum (Hyclone, Utah), penicillin (50 u/ml), streptomycin (50 $\mu$g/ml), and 2 mM glutamine (Sigma) (RPMI-CM). PBMC were used before or after PHA (Calbiochem, 5 $\mu$g/ml) activation for 3 days in RPMI-CM. Freshly-isolated CD4+ T cell ($2.5 \times 10^4$/well) were added into a flat-bottom 96-well microtiter plate (Costar Corporation, Cambridge, Mass.) coated with anti-CD3 mAb in combination with 4B4 or 9.3 or both as indicated concentration.

Antibody immobilization to culture plates was carried out in phosphate-buffered saline, pH 7.3 (PBS) overnight at 4° C. In some experiments, mAbs were conjugated to magnetic beads (M-450, Dynal) by adding 150 fg of each antibody per bead and added at a ratio of three beads per CD4+ T cell in virus induction studies. Polyclonal CD4+ T cell lines were generated by culturing fresh CD4+ T cells with PHA (5 $\mu$g/ml) and recombinant IL-2 (20 u/ml) (Boehringer, Mannheim, Indianapolis, Ind.) 10 days with replacement of fresh IL-2 every 3 days. CD4+ T cell blasts ($5 \times 10^4$/well) from polyclonal T cell lines were further cultured for 3 days in a 96-well plate in the presence of co-stimulatory antibodies as described above. Human 4-1BB cDNA transfected Jurkat cells (J8-1) were prepared, and maintained in RPU-CM.

Flow-Cytometry Analysis

Cells were stained and analyzed on FACScan (Becton Dickinson), as described previously (21). Briefly, fresh cells were washed once and cultured cells 3 times in PBS containing 1% BSA. Approximately $2.5-5 \times 10^5$ cells were re-suspended in 200 $\mu$l PBS-1% BSA with diluted mAbs and incubated on ice for 30 minutes. After washing twice, cells were fixed with 1% paraformaldehyde. Flow cytometry analysis was carried out on lymphocyte-gated cells based on forward-versus-side scatter profiles.

Proliferation Assay

The cells in quadruplicate wells were stimulated for 5 days and then pulsed for 6 hrs with [$^3$H] thymidine (TdR) (NEN, Boston, Mass.) at 1.0 $\mu$ci/well. The stimulation index was calculated by dividing the counts per minute (CPM) of [$^3$H] of stimulated cells by those of unstimulated cells.

RT Activity Assay

Virion-associated reverse transcriptase (RT) activity was measured as described by Willey et al., (J. Virol. 1988, 62:139–47), with modification as follows: 5 μl of 7-day culture supernatants were added in triplicate to 25 μl of a mixture which contained a template primer Poly(A) (5 μg/ml), Oligo(dT) (1.57 μg/ml) (Pharmacia) and 10 μg [$^3$H] dTTP (Amersham Corp., Arlington Heights, Ill.) in 50 mM Tris, pH 7.8, 7.5 mM MgCl$_2$, 2 mM DTT. After incubation for 2 hrs at 37° C., 6 μl of the mixture was spotted onto DE81 paper, air-dried and washed five times in 2×SSC buffer and two additional times in 95% ethanol. The papers were dried, cut and counted on a scintillation counter.

Gene Transfection and Chlorampenicol Acetyltransferase (CAT) Activity Assay

Human Jurkat T lymphocytes and 4-1BB-transfected subline, J8-1, were transiently transfected with PHIV-1-LTR-CAT plasmid (20 μg/10$^7$ cells) by DEAE-Dextran method as described by Bressler (J. Immunol., 147:2290–94, 1991). Luciferase genes were co-transfected for normalization. After 24 hr post-transfection, the cells were stimulated with immobilized mAbs as indicated or PHA (5 μg/ml) plus PMA (10 ng/ml) for 24 hr prior to harvest. Whole-cell extracts were prepared from transfectants and chioramphenicol acetyltransferase (CAT) activity were performed in a final volume of 150 iii containing 0.1 μci (3.7 KBq) of $^{14}$C-chloramphenicol, 4 mM butyl-coenzyme A and 0.25 M Tris-HCl pH 7.4 at 37° C. overnight. The results are given in percent conversion of chloramphenicol to its monoacetylated forms. Values were obtained from 4 independent transfections following normalization with luciferase activities.

Statistical Analysis

Data are presented as means±SD. Two-tailed Student's t-test was used to determine the significance of the differences between groups. Correlation was calculated using a "r" linear correlation coefficient.

Results

Expression of 4-1BB on CD4+ and CD8+ T cells from HIV-I PBMC

Clinical correlation. Forty HIV-1-infected subjects and twelve-seronegative controls were examined for 4-1BB expression on T cells by immunofluorescent cytometry.

The expression levels of 4-1BB were not detectable on unstimulated T lymphocytes either from HIV-1-infected or control individuals prior to in vitro stimulation. After PHA stimulation, the percentage of 4-1BB expressing cells was significantly higher in HIV positive individuals than in the HIV-1 negative control individuals. It should be noted that not only the level of 4-1BB expression but also the population of 4-1BB T cells were increased in HIV-1 positive individuals. The distribution of 4-1BB expression on CD4+ and CD8+ T cells within the 3 groups was expressed on 10.9% of CD4+ T cells in HIV-1-controls, whereas 4-1BB was expressed on 28.9% of CD4+ T cells among asymptomatic HIV-1 positive individuals (P<0.01). 4-1BB was expressed on 30.9% of CD4+ T cells in stage IV individuals. The difference in 4-1BB expression between control and stage II/III patient T cells was more profound in CD8+ T cells than in CD4+ T cells. Furthermore, a significant increase of 4-1BB CD8+ T cells was found in stage IV patients (median 47.9%), compared to asymptomatic individuals (P<0.05). In stage II/III individuals, there was a significant correlation in 4-1BB expression between CD4+ and CD8+ T cells (r=0.72 P<0.01). There was also a reverse correlation between absolute CD4+ cell counts and percentage of 4-MB-expressing CD8+ T cells (r=0.63) P<0.05) in all HIV-1 positive individuals.

The Proliferative Response of CD4+ T cells to 4-IBB Co-Stimulation 4-1BB signal alone with CD3 stimulation was not sufficient for the proliferation of the primary T cells. Therefore, the synergistic effects of anti-4-IBB with anti-CD28 mAb were tested, and the proliferation of CD4+ T cells from 3 HIV-1-healthy donors was measured through the use of serially diluted anti-CD28 (0 to 10 μg/ml) with or without anti-4-1BB (10 μg/ml) were immobilized on tissue culture plates, with anti-CD3 mAb (1 μg/ml). The CD4+ T cells were cultured with the mAbs for 5 days and cell proliferation was measured by [$^3$H] TdR uptake. It was found that 1 μg/ml of anti-CD28 mAb was able to synergize with 4-1BB co-stimulatory activity. Based on these results, the combined anti-CD28 (1 μg/ml) and anti-4-1BB mAb (10 μg/ml) were used to investigate the 4-1BB co-stimulatory function on CD4+ T cell proliferation from HIV-1 positive individuals. The CD4+ T cells purified from PBMC from 9 HIV-1 positive individuals (CD4+ counts: 468±142) were examined for proliferation after 5-day cultures. 4-1BB signal alone showed nearly no stimulatory activity in CD4+ T cells of HIV-1 positive individuals. However, CD4+ T cell proliferation occurred with 4-1BB cross-linking when suboptimal stimulation through CD28 was added. In addition, it was determined that the CD4+ T cell proliferative responses were lower in HIV-1 infected individuals compared with HIV-1 individuals. Furthermore, the lower proliferation corresponded to lower CD4+ T cell counts.

H4-1BB Co-Stimulation and HIV-1 Production

To study the effect of 4-1BB co-stimulation on HIV-1 production in CD4+ T cell, the CD4+ T cells by plate-bound or bead conjugated mAbs, as described in Materials and Methods were stimulated. HIV-1 production was measured by reverse transcriptase (RT) activity and cell proliferation was measured by [$^3$H] TdR uptake as designated by a stimulation index (SI). The positive threshold of RT activity was set by the values higher than the median of negative controls by 3 standard deviations. Table 1 summarizes the results from the 6 HIV-1+ patients who had a positive virus replication (from at least one of the stimulation groups) among 10 tested individuals. The proliferation index of some groups was not determined, because nearly no cells survived in these groups after 7-day culture. In two patients, RT activity was detected only from the combined CD28 and 4-1BB co-stimulation group, but not from CD28 alone group, although both groups showed a similar stimulation index. In three patients, RT activity was similar or slightly higher in the combined CD28 and 4-1BB co-stimulation groups, compared with CD28 co-stimulation alone. In all these 6 patients, no virus was detected from CD3 stimulation or CD3 stimulation with 4-1BB co-stimulation groups.

It was also found that most of the CD4+ T cells which produced virus after stimulation were from patients of lower CD4 counts. Table 2 shows data from 6 of 9 patients whose T cells were stimulated with mAbs conjugated to Dynal M450 beads and produced RT activity from at least one of the stimulation groups. Compared with plate-bound mAb stimulation, the stimulation mediated by bead-conjugated mAbs was higher in levels of RT activities, perhaps indicating that mAbs immobilized on beads gave stronger signals. Bead-conjugated mAb stimulation could make cells proliferate even in CD3 and CD3 plus 4-1BB stimulation group. It became, therefore, possible to observe the function of 4-1BB co-stimulation alone in virus replication. As shown in Table 2, the combined CD28 and 4-1BB co-stimulation produced virus from CD4+ T cell cultures from all donors. The RT activity increased from 1.2-fold to 1 1-fold by combined co-stimulation of CD28 and 4-1BB compared to CD28 co-stimulation alone. Similar results were obtained when another anti-4-1BB mAb (BBK-4) were used in 2 donors (data not shown).

Importantly, the virus was also detected in co-stimulation with anti-4-IBB mAb alone, although the stimulation index was very low after 7-day culture in these groups. The data summarized in Tables 1 and 2 suggest that co-stimulation via 4-1BB results in CD4+ T cell activation and subsequently, enhances virus production. These activation signals for HIV-1 production may coincide with those that mediate the proliferative response.

4-1BB Co-Stimulation and Virus Replication in Polyclonal CD4+ T Cell Lines from HIV-1+ Individuals To further confirm the findings that 4-1BB signal enhanced HIV-1 replication in CD4+ T cells from HIV-1-infected individuals, polyclonal CD4+ T cell lines were generated from 6 HIV-1+ asymptomatic individuals by stimulation with PHA and IL-2 for 10 days. No, or very low RT activities were detected from the culture supernatants. These cells were subsequently stimulated with immobilized anti-CD3 mAb and additional co-stimulatory antibodies for 3 days. The virus level was significantly higher in 4-1BB co-stimulation than anti-CD3 mAb stimulation alone (P<0.05). In contrast, although the virus level was higher in CD28 co-stimulation group than in CD3 stimulation group, no statistical significance was found between these two groups. In this study, the proliferation Index were almost the same in all of these groups. These results from polyclonal CD4+ T cell lines are consistent with those obtained from primary CD4+ T cell stimulation which presented in Tables 1 and 2. Taken together, the data suggest that 4-1BB co-stimulation enhances virus production in HIV-1-infected CD4+ T cell cultures.

4-IBB Ligation Enhances LTR-driven Transcription in Jurkat Cell Line

The J8-1 cell line is a subline of Jurkat, and is a 4-IBB-transfectant that expresses a high level of 4-1BB constitutively. J8-1 was transiently transfected with pHIV-1+-LTR-CAT and subsequently activated with immobilized co-stimulatory mAb or PHA plus PMA. The parental Jurkat cells which express no detectable 4-1BB by flow cytometry were used as negative controls. The level of CAT activities in stimulation groups was shown as fold over unstimulated control. A 1.9-fold increase in CAT activity was observed in immobilized anti-CD3 mAb stimulation in J8-1 compared with isotype control. Anti-4-IBB mAb by itself did not increase the CAT activity in JS-1. However, when combined with immobilized anti-CD3 mAb, anti-4-IBB mAb gave a 5.8-fold increase in CAT activity compared with isotype control or a 3.2-fold increase compared with anti-CD3 mAb stimulation alone. 4-1BB stimulation had an additional effect on CD3 plus CD28 combined stimulation. In the parental Jurkat cell, 4-1BB co-stimulation produced 1.2-fold more CAT activity compared with anti-CD3 mAb alone. These slight increases of CAT activity from 4-1BB co-stimulation in parental Jurkat cells may come from the small amount of 4-1BB expression induced during activation. From these data, it was shown that 1) H4-1BB co-stimulation with TCR/CD3 enhances transcription of the HIV-1 LTR; 2) 4-1BB provides additional stimulatory effect on HIV-1-LTR to anti-CD3 plus anti-CD28 stimulation.

The results of this data indicate that the relative proportion of T cells expressing 4-1BB both in CD4+ and CD8+ T cells is increased from HIV-1-seropositive individuals after PHA stimulation, and relative expression of 4-1BB on CD8+ T cells is correlated to CD4+ T cell counts, which may be related to disease severity and progress. The 4-1BB molecule was expressed rapidly and reached its peak between 48–72 hrs. The levels of expressed H4-1BB began to decrease by 72 hrs post-stimulation and eventually went back to normal levels. Once these cells were reactivated, it was determined that the level of 4-1BB on each cell and the number of 4-1BB expressing cells increased.

During HIV-1 infection, at an early stage after HIV antigen stimulation, T cells are primed, but after several weeks, some of them acquire characteristics of memory cells, and continue to express the same set of activation markers. This set of markers includes: HLA-DR and CD38. These may account for the finding that no 4-1BB expression was found on resting T cells, which is itself related to the continuous activation and death of CD4+ 4-IBB+ T cells in response to HIV-1 antigen in vivo. The increased 4-1BB expression on T lymphocytes of HIV-1-infected individuals after in vitro stimulation would then reflect not only the current state of immune activation in HIV-1 infection, but also the state of memory-primed cells challenged by HIV-1 antigen during acute infection in vivo. The increased 4-1BB expression on CD4+ T cells after re-stimulation is related to the increase of virus replication. In HIV-1 infection, CD8+ T cells, play a role in suppressing HIV-1 replication through the classical HLA-restricted cytolysis of infected cells and non-cytolytic mechanism that involves some secreted CD8-cell antiviral factors. 4-1BB, as a co-stimulatory molecule, with its increased expression on CD8+ cells in HIV-1 infection, may relate to CD8+ T cell proliferation and antiviral function. In HIV-1 patients, CD8+ T cells generally proliferate more vigorously than. CD4+ T cells when the cells were stimulated with anti-4-1BB mAb.

Ligation of CD28 with soluble mAb in the presence or absence of soluble anti-CD3 has been reported to induce virus from CD4+ T cells prepared from HIV-1-infected donors. Activation of CD4+ T cells from HIV-1 positive donors with immobilized anti-CD3 and anti-CD28 mAb, however, induced a virus-resistant state. This effect was specific for macrophage-tropic HIV-1 and appears to be the result of down-regulation of CCR5, the fusion cofactor. Although no statistically significant difference was found, the ligation of CD28 with immobilized 9.3 did increase HIV-1 replication from some HIV-1 infected donors. This observation, which differs from other reports, may be because of the methods of immobilization of anti-CD3 or anti-CD28 mAb on the beads. Studies using bead-immobilized mAbs showed that the additional signal from 4-1BB enhanced virus replication from primary CD4+ T cells from HIV-1 positive individuals. Because the exact amount of anti-CD28 mAb and anti-CD3 mAb were used in combined CD28 and 4-1BB co-stimulation and CD28 co-stimulation groups, the enhancement of virus production should be considered from additional 4-1BB signaling.

Furthermore, virus was induced by 4-1BB co-stimulation alone. In some donors, the virus levels were even higher than that by CD28 co-stimulation, although the stimulation index of primary CD4+ T cells in response to 4-1BB co-stimulation was very low. In polyclonal CD4+ T cell lines, a statistically significant difference of virus replication was found between 4-1BB co-stimulation and CD3 stimulation alone. This comparison was based on the similar stimulation index (SI) within each group. From the present studies, it was shown that cross-linking of 4-1BB and CD3 in CD4+ T cells from HIV-1+ individuals induced virus production. The function of 4-1BB co-stimulation on virus production was not correlated with the function on T cell proliferation, perhaps suggesting that the cellular pathways that mediate HIV-1 induction might be similar, but not identical, to those of mitogenic stimulation.

A number of factors have been reported to up-regulate HIV-1 expression in vitro. Many of these agents including TNF-α, anti-CD30 mAb, HIV Tat protein, activate HIV-1 transcription through the NF-κB enhancer present in the HIV-1-LTR. In the experiments done it was shown that, HIV-1-LTR transactivation had been obtained by a combination of anti-CD3 and anti-4-1BB mAb. These results suggest several potential roles of 4-1BB in HIV-1 pathogenesis: (1) 4-1BB directly upregulates the transcription of the viral genome in latently infected cells; (2) 4-1BB and 4-1BB ligand interaction may activate virus replication of CD4+ T cells in the presence of antigenic stimuli; (3) 4-1BB co-stimulation may activate resting CD4+ T cells and as a consequence, promote an efficient propagation of newly produced virions that preferentially infect activated CD4+ T cells; (4) 4-1BB-mediated signals to HIV-1 infected CD4+ T cells may bind to apoptosis, resulting in premature death of infected cells.

The results demonstrate that 4-1BB expression was increased in HIV-1 infected PBMC after in vitro activation correlating to immune activation and disease progress. Ligation of 4-1BB in HIV-1 infected CD4+ T cells enhanced virus replication in vitro, as mediated through an NF-κB pathway. If the 4-1BB co-stimulatory pathway is disturbed or purposely interfered with at early stages of the infection it is likely that a lower virus load will result. This in turn will serve to prevent the subsequent loss of CD4+ T cells, and maintain immune competency. The increased 4-1BB expression on CD8+ T is correlated to the degree of immunodeficiency in HIV-1 infection.

EXAMPLE 5

Role of 4-1BB in Human CD4+ T cell Adhesion

The human 4-1BB protein is a co-stimulatory molecule for T cells. By studying the role of 4-1BB in T cell adhesion with human primary T cells and two T cell lines, CEM and Jurkat, it was discovered that 4-1BB co-stimulation induced T cell adhesion dramatically. Anti-4-1BB signaling along with PMA/ionomycin stimulation caused CEM cells, which express a high level of 4-1BB, uncharacteristic cell adhesion. In contrast, Jurkat cells which do not express a detectable level of 4-1BB demonstrated nearly no response to anti-4-1BB in cell adhesion to fibronectin (FN). When Jurkat cells were transfected to produce 4-1BB, they acquired the ability to adhere in response to FN by anti-4-1BB stimulation. An absolute co-requirement for anti-CD3 stimulation in addition to 4-1BB signaling to cell adhesion in the Jurkat transfectants suggests that adhesion caused by anti-4-1BB is mediated through activation of adhesion signaling rather than a direct interaction between 4-1BB and FN or anti-4-1BB. It is in this way that the 4-1BB co-stimulatory signal amplifies T cell activation, by intermediating CD28 co-stimulation with adhesive responses.

Antibodies and Reagents for Adhesion Studies

Monoclonal anti-4-1BB, BK4, also called 4B4-1 (mouse IgG) was used to stimulate and immunostain 4-1BB on T cells. The anti-4-1BB was conjugated with biotin for flow cytometric analysis. Anti-CD28, mAb 9.3 (mouse IgG2a) was a kind gift from Dr. C. H. June (Naval Medical Research Institute, Bethesda, Md.). Monoclonal anti-CD3 (OKT3) was purchased from Ortho Diagnostic (Westwood, Mass.). Secondary cross-linking goat anti-mouse IgG (H+L) was purchased from Zymed (South San Francisco, Calif.). Blocking anti-integrin $b_1$, purchased from Immunotech (Westbrook, NEE). 4-1BB-Fc, a fusion protein consisting of the extracellular portion of human 4-1BB coupled with the Fc region of human $IgG_1$ was obtained from Immunex (Seattle, Wash.) An isotype control mouse $IgG_1$ (MOPC-21) conjugated with biotin was purchased from PharMingen (San Diego, Calif.). Human fibronectin was obtained from Dr. Fred Pavalko (Indiana University). A premixed cocktail of monoclonal antibodies and complement to isolate T cells was purchased from One Lambda (Canoga Park, Calif.).

Flow Cytometry

Selected T-cells were stimulated and re-stimulated with anti-CD3 and anti-CD28 for 3 days and used for proliferation and adhesion assay in response to different co-stimulatory mAbs. CEM, a human leukemic T cell line, was stimulated with PMA (10 ng/ml) and ionomycin (IgM) for 24 hr before adhesion assay. Jurkat human leukemic T cell line was transfected with pcDNA3 with entire 4-1BB cDNA and selected for neomycin resistant clones by limit dilution. 4-1BB expression levels on the cell surface of the transfectants were determined by flow cytometry.

T cells ($2 \times 10^5$ cells) were suspended in 200 ml of 2 µg/ml anti-4-1BB conjugated with biotin in staining solution, PBS containing 1% bovine serum albumin (BSA) and incubated at 4° C. for 30 minutes. The cells were subsequently washed three times, re-suspended in 200 ml of phycoerythrin (PE) conjugated streptavidin, 1 µg/ml, and incubated for 30 minutes. After wash, the samples were fixed with 1% paraformaldehyde prior to flow cytometric analysis on the FACScan (Becton Dickinson, Mountainview, Calif.). Biotin-conjugated mouse IgG (MOPC-21, PharMingen, San Diego, Calif.) was used for isotype control for anti-4-1BB conjugated with biotin. Gates were set on live cells based on forward versus side scatter profiles. 10,000 events were collected for each sample.

Immobilization of antibodies and FN to microtiter plates 96-well flat bottom polystyrene plates (Costar, Cambridge, Mass.) were coated overnight at 40° C. with anti-4-1BB, anti-CD28, at 10 µg/ml in PBS or otherwise at the concentrations indicated in the text. In some cases, the antibody solution was included with FN or BSA as a control at 0.1 µg/ml each. The plates were then rinsed to remove non-adherent proteins and cells were immediately added to the plates after final wash. To block anti-4-1BB, the T cells were labeled with [−5'Cr] sodium chromate, 200 µg/ml at 37° C. for 1 hr, and transferred to 96-well plate ($5 \times 10^1$ cells/well) coated with anti-CD28, anti-4-1BB or both anti-CD28 and anti-4-1BB.

For adhesion assays for primary and Jurkat cells, the plates coated with FN in addition to the antibodies were used. After cells were incubated at 37° C. in a carbon monoxide incubator for the indicated time periods, unbound cells were removed by washing the plates with prewarmed culture medium three times and the cells remained bound to plates were lysed in 1% sodium dodecylsulfate (SDS). The lysates were counted for radioactivity and the percentage of bound cells were calculated as a ratio bound to total cpm added to the wells. The adhesion assay for CEM cells were undertaken in the plates where FN was omitted in antibody coating. The adhesion assay for the Jurkat 4-1BB transfectants was performed in the presence or absence of soluble anti-CD3 at 1 μg/ml.

Assays for Proliferation

The primary T cells which were repeatedly stimulated with anti-CD3 and anti-CD28 as described above were subjected to further activation by soluble anti-CD3, 1 with secondary anti-mouse IgG, 5 μg/ml in the 96-well plates previously coated with co-stimulatory anti-CD28 or anti-4-1BB or with with anti-CD28 at 10 μg/ml plus additional anti-4-1BB at indicated concentrations. In some cases, the cells were co-stimulated with immobilized co-stimulatory antibodies including sub-optimal 0.1 μg/ml FN. After 3 days, proliferation rates were measured by 6-hr pulse-labeling with [$^3$H] thymidine, 1.0/well.

4-1BB signal induced uncharacteristic cell adhesion of PMA/ionomycin-stimulated CEM cells to culture plate. Although both CD28 and 4-1BB are able to co-stimulate T cells similarly for proliferation and IL-2 production, one obvious difference of the two molecules is their expression modes. 4-1BB expression is highly regulated as compared to CD28 which expresses constitutively in the most of T cells. The 4-1BB molecule from most of the CD4+ human lymphoma was not detected. The T cell lines which were tested included Jurkat, CEM, Molt-4, and HUT-78. However, CEM cells were exceptional in readily inducing 4-1BB upon PMA/ionomycin stimulation to an extremely high levels compared to those induced by activated primary T cells. CEM cells became blastic and aggregated after PMA/ionomycin stimulation, but remained non-adherent to culture plate.

During the experiments it became clear that the stimulated CEM cells responded vigorously to plate-bound anti-4-1BB completely spreading to culture plate. The responses were so intense that no extraneous stimulating adhesion receptor ligands were necessary. More than 80% of the PMA/ionomycin-stimulated CEM cells were firmly attached to culture plates in response to anti-4-1BB within 1 hr. On the contrary, the CEM cells which were not previously stimulated and, therefore, produced no detectable 4-1BB did not respond to anti-4-1BB at all. Since CD28 is a primary co-stimulatory molecule, CEM cell response to anti-CD28 was tested to determine whether this induction of CEM adhesion was unique to 4-1BB co-stimulation. In contrast to anti-4-1BB, anti-CD28 did not induce cell adhesion for both stimulated and un-stimulated CEM cells.

The distinctive co-stimulatory outcomes from 4-1BB and CD28 in CEM cell adhesion indicate that the two co-stimulatory molecules deliver non-overlapping signals. Several anti-CD4 mAbs whose antigens are abundant on CEM cell surface but observed no such responses as seen with anti-4-1BB were tested. The 4-1BB signal altered morphology of CEM cells. It was also determined that noticeable morphological changes in CEM cells immediately following firm attachment to culture plates in response to anti-4-1BB. The CEM cells remained in dispersed form during culture and usually became clustered after PMA/ionomycin stimulation. There were dramatic changes in cell shape when the stimulated cells were exposed to immobilized anti-4-1BB. Anti-4-1BB signal following PMA/ionomycin stimulation completely altered the round cells to elongated fibroblastic shapes with sharp spikes. This observation suggest that 4-1BB signal may induce cytoskeletal rearrangement which can allow the cells to adapt to cell adhesion to culture plate. A similar morphological change with anti-CD28 was not observed.

The adhesion and morphological changes caused by anti-4-1BB, however, did not affect cell proliferation rate. 4-1BB co-stimulatory signal induced Jurkat cell adhesion to FN. Although CEM cells provided a good model for eliciting 4-1BB roles in T cell activation, there were obstacles for interpreting the results mainly because of PMA/Ionomycin stimulation to produce 4-1BB during 4-1BB stimulation. The simultaneous multiple signals made difficult to discern the 4-1BB action responsible for the final outcomes. To circumvent the problem, stable T cell transfectants that constitutively expressed 4-1BB without prior stimulation to induce 4-1BB expression were developed. Jurkat cells did not express detectable level of 4-1BB. Jurkat cells were transfected to produce 4-1BB with 4-1BB cDNA inserted in expression plasmid pcDNA3. After G418 selection, three transfectant clones producing different levels of 4-1BB, 17-2,8-1 and 2-7 from lowest to highest in order, were obtained. The 4-1BB expressions of the parental and each Jurkat transfectant measured by flow cytometry are shown in. The 4-1BB expression level of the highest 4-1BB producer, transfectant, 2-7 was still about 10 times lower than those seen in CEM. Therefore, parental Jurkat and these transfectants for 4-1BB-mediated cell adhesion to plate-bound a sub-optimal FN (0.1 μg/ml) which primarily supports integrin-mediated adhesion in T cells were used.

The cell adhesion assay was performed using the plates coated with isotype control $b_1$, anti-CD28, anti-4-1BB or both anti-CD28 and anti-4-1BB in addition to FN and measured the cells attached to the plate after 1–5-minutes in culture at 37° C. with or without soluble anti-CD3. The 4-1BB transfectants but not parental Jurkat cells promptly responded to anti-4-1BB only in the presence anti-CD3. The data from the Jurkat 4-1BB transfectants clearly indicated that cell adhesion in response to anti-4-1BB occurred in a 4-1BB expression level-dependent manner. The highest response was seen in tranfectants 2-7 but lowest in transfectant 17-2. Under the same conditions, the control Ig and anti-CD28 mAbs. At saturation concentration did not induce such cell adhesion for the all the cells tested.

To examine whether 4-1BB and CD28 signals interact each other, the level of cell adhesion in the presence of both anti-4-1BB and anti-CD28 was determined. The two co-stimulatory signals resulted in synergistically higher cell adhesion. Therefore, 4-1BB appears to require CD28 signalling for maximal adhesion response. The anti-4-1BB-mediated adhesive responses detected in the presence of anti-CD3 were totally abolished when anti-CD3 was absent. The critical requirement of anti-CD3 in 4-1BB-mediated cell adhesion indicates that this cell adhesion was not caused simply by an interaction between 4-1BB and anti-4-1BB or FN but rather intermediate CD3 signaling to cell adhesion pathways. Taken together, 4-1BB and CD28 are both co-stimulate T cells but the 4-1BB roles are different form CD28 in inducing T cell adhesion to FN. The cell adhesion through anti-4-1BB signal did not change proliferation rate in Jurkat cells as seen in CEM. 4-1BB expression progressively increased by repeated CD3 activation. The link with previous studies and human peripheral T cells was strengthened through a series of flow cytometry experiments with 4-1BB expression patterns during anti-CD3 activation.

The expression levels of 4-1BB are detected only in about 2% of the T cells freshly prepared from healthy individuals. The levels were increased through repeated in vitro anti-CD3 and anti-CD28 activation. T cells stimulated with anti-CD3 and anti-CD28 for 3 to 4 days exhibited about 20% cells in 4-1BB positive but the levels were gradually declined following the peak. The numbers of activated cells in IL-2 without anti-CD3 and anti-CD28 was expanded. The 4-1BB expression levels were progressively decreased during the culture in IL-2. However, a dramatic increase of 4-1BB both in the cell number in 4-1BB positive and the expression levels were obtained upon re-stimulation with anti-CD3 and anti-CD28 resulting in greater than 50% of the cells positive with 4-1BB. The repeated cycles of stimulation progressively increased 4-1BB expression levels even higher when additional anti-4-1BB signal is added to anti-CD3 and anti-CD28 stimulation. These observations suggest that the 4-1BB- producing cell population may be in proliferative advantage due to additional 4-1BB co-stimulatory input during repeated stimulation.

A large portion of T cells still registered expression of 4-1BB even after prolonged activation with respect to 4-1BB expression. 4-1BB signaling induced primary T cell adhesion mainly through integrins. The human primary T cells activated by two 3-day consecutive cycles of stimulation with anti-CD3 and anti-CD28 were prepared to increase 4-1BB expression on the cells. The cells were maintained for 7 days in IL-2 prior to re-stimulation. Following each stimulation step, a determination was made as to whether the activated primary T cells could be induced for cell adhesion to sub-optimal FN by 4-1BB signal as observed in CEM and Jurkat cells. The percentages of the cells attached to the plates coated with anti-CD28 or anti-CD28 and anti-4-1BB in addition to sub-optimal FN at 0.1 $\mu$g/ml in the presence of soluble anti-CD3 after 1 hr was determined. While anti-CD3 alone or anti-CD3 and anti-4-1BB induced negligible adhesion to FN, anti-CD28 co-stimulation resulted in about 16% bound to the sub-optimal FN-coated plate. However, a dramatic increase in cell adhesion was seen when the activated T cells were co-stimulated by both anti-4-1BB and anti-CD28 resulting in 50% of the cells firmly attached to the plates after 1 hr. Considering that only about 50% of the stimulated T cells used in the assay expressed 4-1BB, the cell adhesion observed may have been the maximum levels achievable.

The cells further activated by repeated re-stimulation gradually lost the responsiveness to signal anti-CD28 alone significantly but not to the combined signals from both anti-CD28 and anti-4-1BB. Integrins, mainly (X401 (CD49d/CD29) and $a_5b_1$ (CD49e/CD29) are primary adhesion molecules responsible to transmit the FN interaction. To determine whether 4-1BB-induced cell adhesion to FN was mediated by the integrins, the cells were incubated with blocking mAb to integrin $b_1$ before adhesion assays. The adhesion induced by anti-4-1BB was effectively inhibited by more than 50% as a result of the pretreatment with anti-integrin. The results suggest that 4-1BB may activate integrins to promote FN interaction rather than involve in direct association with FN. Murine 4-1BB has been known to have strong affinity to FN but the direct interaction between 4-1BB and FN does not seem to be a major force in this cell adhesion. The FN augmented synergistic 4-1BB effects on CD28 co-stimulation. Because 4-1BB and CD28 cooperated for promoting T cell adhesion to FN, a determination was made as to whether cell adhesive response affect the synergy between 4-1BB and CD28 signals for proliferative responses.

It was hypothesized that if 4-1BB worked cooperatively with CD28 was mediated by cell adhesion, the 4-1BB effect should be further amplified by FN. In fact, it has been shown that FN itself can co-stimulate T cells reducing antigen threshold for T cell activation. To test the possibility, the effects of FN in proliferative responses of the activated primary T cells co-stimulated by anti-CD28, anti-4-1BB, or both antibodies were determined. To maximize the anti-4-1BB effects, a sub-optimal anti-CD28 concentration at 0.5 $\mu$g/ml was selected because it leads only marginal proliferation by anti-CD3. Under the conditions, a determination was made with regard to the anti-4-1BB effects on anti-CD28-mediated proliferation with or without FN. Anti-4-1BB alone co-stimulate highly purified human T cells with anti-CD3 modestly. However, anti-4-1BB allowed the sub-optimal anti-CD28 to lead high proliferative response indicating that there was a definite cooperation between CD28 and 4-1BB in co-stimulation. Next addressed was whether this 4-1BB cooperation with CD28 can be amplified by FN. The results of the experiments clearly demonstrate that the synergistic cooperation between CD28 and 4-1BB was greatly enhanced by FN. The sub-optimal FN concentration used in the experiment effected little for CD28 or 4-1BB co-stimulation. The cells under sub-optimal CD28 and FN influences were able to fully respond to anti-CD3 activation by the presence of 4-1BB signal. This indicates that the primary role of 4-1BB is to sensitize T cells to respond to antigenic activation by integrating TCR co-stimulation and cell adhesion.

The anti-4-1BB effects on amplifying T cell proliferative response were totally abolished when 4-1BB-Fc, a competitive blocking reagent to 4-1BB was included in the culture indicating the specificity of the anti-4-1BB. 4-1BB signaling reduced threshold of CD3 signal required for CD28 co-stimulation. co-stimulatory signal can reduce antigen threshold. The strengthened co-stimulatory input may reduce the threshold of antigen stimulation. To determine whether synergistic 4-1BB effects on CD28 co-stimulation could further reduce the threshold of CD3 signal, a titration of the anti-CD3 concentrations necessary for activating T cells as measured by proliferation, was measured.

Activated primary T cells were proliferated by varying anti-CD3 concentrations, 0.01, 0.1 and 1 mg/ml under the different co-stimulatory conditions by anti-CD28, anti-4-1BB or both anti-CD28 and anti-4-IBB. The 4-1BB synergistic effects on CD28 co-stimulation allowed high proliferation with 0.1 mg/ml of anti-CD3, which would lead to relatively low proliferative response if the cells were co-stimulated with either anti-CD28 or anti-4-1BB alone. Such a high proliferative response was achieved by more than 10 fold higher anti-CD3 (1 mg/ml) when the cells were co-stimulated by anti-CD28 alone. Therefore, effective anti-CD3 concentration could be reduced by fold by 4-1BB engagement to CD28 co-stimulation. The anti-4-1BB co-stimulation alone, however, resulted in modest proliferation. The results demonstrate that the 4-1BB signal gave rise a pronounced impact in reducing threshold of anti-CD3 by cooperating with CD28.

To verify 4-1BB effects on CD28 co-stimulation, the T cell proliferative responses 0.1 mg/ml anti-CD3 under the co-stimulation with increasing amounts of anti-4-1BB at the fixed anti-CD28 concentration at 10 mg/ml were measured.

The results showed that the synergistic 4-1BB effects on CD28 co-stimulation was dose-dependent manner. Therefore, it was shown that 4-1BB signal synergized CD28-mediated T cell activation by enhancing adhesive response thereby being able to allow high proliferative responses with the lower anti-CD3 concentration. This 4-1BB function may be important for the T cells needed being continuously activated or survived in limited co-stimulatory signals during chronic immune reaction. In particular, 4-1BB role may be crucial in amplifying cytotoxic T cell responses to eradicate weakly immunogenic tumor cells which often down regulates T cell immune surveillance. Promoted adhesive responses by 4-1BB may be a key intermediating pathways responsible for 4-1BB-mediated amplification in CD8+ T cell cytotoxicity for tumor cells.

T Cell Integrin Activation

Up-regulation of integrin activity is induced by activation of T cells within minutes, suggesting a qualitative alteration in function of the integrin receptor. The integrins co-stimulate T cells activated by sub-mitogenic levels of anti-CD3 in the presence of FN or other appropriate ECM proteins. Integrins $a_4b_1$ and $a_5b_1$ which bind to fibronectin (FN) or vesicular cell adhesion molecule-1 (VCAM-1), characteristically play a predominant role in mediating FN co-stimulated T cell proliferation and intracellular $CA^{+2}$ signaling. FN mediated adhesion of T cells indicates activation and avidity of integrin.

The receptors which activate T cells include CD3/TCR complex and CD2, CD7, CD28 and chemokines. Treatment of T cells with phorbol ester, PMA or Ca+ ionophore, ionomycin also up-regulates integrin activity, implicating both protein kinase C and intracellular calcium with this regulatory events. Integrins are associated intracellular cytoskeletal proteins and termini of actin stress fiber bundles in cell attachment structures known as focal adhesions. Stimulation of the integrins ultimately leads to Rho-dependent focal adhesion formation that is accompanied by the tyrosin phosphorylation of paxillin as well as changes in the activity of the members of FAK, Src and Csk. Cross-linking of CD28, a glycoprotein on T cells also results in increased adhesion to FN. VCAM-1 and intercellular adhesion molecule-1 (ICAM-1). CD28-mediated regulation 1:1 of $b_1$-integrin-dependent adhesion involves the association of phosphatidylinositol-3-kinase (PI 3-K). CD28 has been well characterized as a co-stimulatory molecule for T cell activation, regulating IL-2 gene expression.

The 4-1BB effects on cell adhesion absolutely required anti-CD3 activation but not anti-CD28. Thus, 4-1BB function is tightly controlled by antigenic activation. There was synergy between CD28 and 4-1BB signals in Jurkat cell adhesion and thus the 4-1BB signal may function to complement CD28 co-stimulation for downstream pathways facilitating the TCR signal to adapt to inside-out adhesive responses.

Following the initial activation of primary T cells, a series of adhesive responses to cell specific ligands or ECM also co-stimulate T cell proliferation. Integrin activation requires TCR signal to enhance avidity to their ligands. The expression of both 4-1BB and adhesion molecules expression may require prolonged TCR activation, and 4-1BB may activate cell adhesion maintaining the activated T cells to be at high activation stages which enhance 4-1BB expression by positive feedback amplifying loop especially in weak antigen presentation. The expression of 4-1BB was heavily dependent in vitro CD28 co-stimulation and therefore, correlation of 4-1BB and CD28 co-stimulation in primary T cells is more complex to interpret than those in Jurkat 4-1BB transfectants.

The cooperation of the two molecules shown by the essential co-existence of 4-1BB and CD28 in further lowering the threshold of anti-CD3 signal is primarily attributable to the activity of adhesion molecules. Therefore, 4-1BB has the effect of lowering the threshold of antigen receptor signaling, thereby affecting effector T cell function. TCR signaling intensities which is dominantly influenced by co-stimulation, also effects the cytokines such as IF and IL-2 production patterns. The 4-1BB-mediated amplified cytotoxic T cell responses may well result from up-regulated avidity of adhesive molecules on cytotoxic T cells or the ability of the H4-1BB to reduce the antigenic threshold for poorly immunogenic tumors.

Common Abbreviations

| | |
|---|---|
| CTL | cytolytic T lymphocyte |
| HTL | helper T lymphocyte |
| LGL | large granular lymphocytes |
| NK | natural killer cells |
| ConA | concanavalin A |
| DTT | dithiothreitol |
| mAb | monoclonal antibody. |
| 4-1BB | protein expressed on activated T cells |
| rh 4-1BB | recombinant human 4-1BB |
| 4-1BB/L | ligand to 4-1BB found on activatedmacropage and mature B cells |
| 4-1BB/AP | fusion protein between 4-1BB and alkaline phosphatase. |
| SDS | sodium dodecysulfate |
| SSC | 150 mM sodium chloride/15 mM sodium citrate, pH 7.0 |
| TPA | 12-0-tetradecanoylphorbol-13-acetate |
| Th | helper T lymphocytes |
| IL-2 | interleukin 2 |
| IL-3 | interleukin 3 |
| rIL-2 | recombinant IL-2 |
| CSF-GM | granulocyte/macrophage colony-stimulating factors |
| cRNA | complementary RNA |
| ss | single-stranded |
| ds | double-stranded |
| TCR | T-cell antigen receptor |
| PTA | phorbol 12-tetradecanoate 13-acetate |
| r | recombinant |
| mu | murine |
| hu | human |
| BFU-E | burst forming unit-erythroid, an erythroid progenitor cell |
| CFU-GEMM | colony forming unit-granulocyte erythroid macrophage megakaryocyte, a multipotential progenitor cell |
| CFU-GM | colony forming unit-granulocyte macrophage, a granulocyte macrophage progenitor cell |
| CFU-S | colony forming unit-Spleen, a multipotential stem cell |
| H-ferritin | the heavy chain subunit form of ferritin |
| MGF | mast cell growth factor, a c-kit ligand |
| CSF | colony stimulating factors |
| G | granulocyte |
| M | macrophage |
| Epo | erythropoietin |
| IL | interleukin |
| LD | low density |
| NALDT | non-adherent low density T-lymphocyte depleted |
| PMSF | phenylmethylsulfonyl fluoride |
| PBS | phosphate buffered saline |
| AcNPV | *Autographa californica* nuclear polyhedrosis virus |
| SDS | sodium dodecyl sulfate |
| LPS | lipopolysaccharide |

Citations and References Incorporated Herein by Reference

1. Smith, C. A., Davis, T., Anderson, D., Solam, L., Beckmann, M. P., Jerzy, R., Dower, S. K., Cosman, D., 1. and Goodwin, R. G. 1990. A receptor for tumor necrosis factor defines an unusual family of cellular and viral proteins. *Science* 248:1019–1023.
2. Ebina, Y., L. Ellis, K. Jaruagin, M. Edery, L. Graf, E. Clauser, J. On, F. Marizrz, Y. W. Kan, J. D. Goldfine, R. A. Roth and W. J. Rutter, 1985, The human insulin receptor cDNA: the structural basis for hormone-activated transmembrane signalling, *Cell* 40:747.
3. Vassali, R., R. Tedghi, B. Listowska-Bernstein, A. Tartakoff and J. C. Jaton, 1979, Evidence for hydrophobic region within heavy chains of mouse B lymphocyte membrane-bound IgM, *Proc. Natl. Acad. Sci. USA* 76:5515.
4. Haskins, K., R. Kubo, J. White, M. Pigeon, J. Kappler and P. Marrack, 1983, The major histocompatability complex-restricted antigen receptor on T cells I Isolation with monoclonal antibody, *J. Exp. Med.* 157:1149.
5. Lesslaver, W. and H. Gmunder, 1986, Biochemical characterization of the 9.3 antigens of human T-cells: simultaneous expression of disulfide-bonded 90-Kiladalton dimers and free subunits at the cell surface, *Mol. Immunol.* 23:271.
6. Van Lier, R., J. Borst, T. Vroom, H. Klein, P. Mourik, W. Zeijlemaker and C. Melife, 1987, Tissue distribution and biochemical and functional properties of Tp55 (CD27) a novel T cell differentiation antigen, *J. Immunol.* 139:1589.
7. Mallett, S., S. Fossum and A. Barclay, 1990, Characterization of the MRC OX40 antigen of activated CD4 positive T lymphocytes-a molecule related to nerve growth factor receptor, *EMBO J.* 9:1603.
8. Banchereau, J., P. Paoli, A., Valle, E. Garcia and F. Roussel, 1991, Long-term human B cell lines dependent on interleukin-4 and antibody to CD40, *Science* 251:70.
9. Moeller, D. L., M. K. Jenkins and R. H. Schwartz, 1989, Clonal expansion versus functional colonal inactivation: a co-stimulatory signalling pathway determines the outcome of T cell antigen receptor occupancy, *Ann. Rev. Immunol.* 7:445.
10. June, D. H., J. A. Ledbetter, P. S. Linsley and C. B. Thompson, 1989, Role of CD28 receptor in T cell activation, *Immunol. Today* 11:211.
11. Yang, L., B. Jones, A. Aruffo, K. M. Sullivan, P. S. Linsley and C. A. Janeway, Jr., 1992, Heat stable antigen is a co-stimulatory molecule for CD4 T cell growth, *J. Exp. Med.* 175:437.
12. Yamori, T., 1992, Molecular mechanisms for generation of neural diversity and specificity: foles of polypeptide factors in development of post-mitotic neurons, *Neuroscience Res.* 12:545.
13. Liu, Y. J., D. E. Joshua, G. T. Williams, C. A. Smith, J. Gordon and I. C. M. MacLennan, 1989, Mechanism of antigen-driven selection in germinal centres, *Nature*, 342:929.
14. Jabara, H. H., S. M. Fu, R. S. Geha, and D. Vercelli, 1990, CD40 and IgE: synergism between anti-CD40 momoclonal antibody and interleukin 4 in the induction of IgE synthesis by highly purified human B cells, *J. Exp. Med.* 172:1861.
15. Defrance, R., B. Vanbervliet, F. Briere, I. Durnad, F. Roussle and J. Banchereau, 1992, Interleukin 10 and transforming growth factor b cooperate to induce anti-CD40 activated naive human B cells to secrete immunoglobulin A, *J. Exp. Med.* 175:671.
16. Donahue, T., Cigan, A., Pahich, E. and Valavicius, B., Mutations at a Zn(II) finger motif in the yeast e1F-2b gene alter ribosomal start-site selection during the scanning process, *Cell* 54 (1988) 621–632.
17. Carthew, R. W and Rubin, G. M., seven in absentia, a gene required for specification of R7 cell rate in the Drosophila eye, *Cell*, 63 (1990) 561–577.
18. Driscoll, D. M. and Williams, J. G., Two divergently transcribed genes of *Dictyostelium discoideum* are cyclic AMP-inducible and coregulated during development, *Mol. and Cell. Biol.* 7 (1987) 4482–4489.
19. Chalupny, N. J., Peach, R., Hollenbaugh, D., Ledbetter, J. A., Farr, A. G. and Aruffo, A., 1992, *Proc. Natl. Acad. Sci. USA* 89:10360–10364.
20. Noelle, R. J., and Snow, E. C., 1991, *The FASEB J.* 5:2770–2776.
21. Noelle, R. and Snow, E., 1990, *Immunol. Today* 11:361–368.
22. Zurawski, G., Benedik, M., Kamb, B. J., Abrams, J. S., Zurawaki, S. M. and Lee, F. D. (1986) *Science* 232.772–775.
23. Kinachi, T. (1986) *Nature* 325,70–73.
24. Gershenfeld, H. K. and Weissman, I. L. *Science* (1986) 232; 854–858.
25. Biggin, M., Gison; T. and Hung, G. (1983 *Proc. Natl. Acad. Sci. USA* 80,3963–3965.
26. Hodgkin, P. D., Yamashita, L. C., Coffman, R. L. and Kehry, M. R., 1990, *J. Immunol.* 145:2025–2034.
27. Barlett, W. C., McCann, J., Shephaer, D. M., Roy, M. and Noelle, R. J., 1990, *J. Immunol.* 145:3956–3962.
28. Kwon, B. S., Kestler, D. P., Eshhar, Z., Oh, K., and Wakulchik, M. 1989. Expression characteristics of two potential T cell mediator genes. *Cell, Immunol.* 121:414–422.
29. Armitage, R., Fanslow, W., Strockbine, L., Sato, T., Clifford, K., MacDuff, B., Anderson, D., Gimpel, S., Davis-Smith, T., Maliszewski, C., Clark, E., Smith, C., Grabstein, K., Cosman, D. and Spriggs, M., 1991, *Nature* 357:80–82.
30. Kwon, B., Kestler, D., Lee, E., Wakulchik, M. and Young J. (1988) *J. Exp. Med.* (1988).
31. Noelle, R. J., Roy, M., Shepherd, D. M., Stamenkovic, I., Ledbetter, J. A. and Aruffo, A., 1992, *Proc. Natl. Acad. Sci. USA* 89:6550–6554.
32. Hollenbaugh, D., Grosmaier, L. S., Kullas, C. D., Chalupny, N. J., Braesch-Andersen, S., Noelle, R. J., Stamenkovic, I., Ledbetter, J. A. and Aruffo, A., 1992, *EMBO* 11:4314–4321.
33. Schall, T. J., M. Lewis, K. J. Koller, A. Lee, G. C. Rice, G. H. W. Wong, T. Gatanaga, G. A. Granger, R. Lentz, H. Raab, W. J. Kohr and D. V. Goeddel, 1990, Molecular cloning and expression of a receptor for human tumor necrosis factor, *Cell* 61:361.
34. Klein, R., Nanduri, V., Jing, S., Lamballe, F., Tapley, P., Bryant, S., Cordon-Cardo, C., Jones, K. R., Reichardt, L. F. and Barbacid, M., 1991, *Cell* 66:395–403.
35. Armitage, R. J., Sato, T. A., Macduff, B. M., Clifford, K. N., Alpert, A. R., Smith, C. A. and Fanslow, W. C., 1992, *Eur. J. Immunol.* 22:2071–2076.
36. Hintzen, R. Q., deJong, R., Hack, E. E., Chamuleau, M., de Vries, E. F. R., ten Berge, I. J. M., Borst, J. and van Lier, R. A. W.; 1991, *J. Immunol.*, 147:29–35.
37. Mallett, S., and Barclay, A. N. 1991. A new super-family of cell surface proteins related to the nerve growth factor receptor. *Immunol. Today.* 12:220–223.
38. Kwon, B. S., and Weissman, S. M. 1989. cDNA sequences of two inducible T-cell genes. *Proc. Natl. Acad. Sci. USA.* 86:1963–1967.
39. Johnson, D., Lanahan, A., Buck C. R., Sehgal, A., Morgan, C., Mercer, E., Bothwell, M., and Chao, M. 1986. Expression and structure of the human NGF receptor. *Cell* 47:545–554.

40. Stamenkovic, I., Clark, E., and Seed, B. 1989. A B-lymphocyte activation molecule related to the nerve growth factor receptor and induced by cytokines in carcinomas. *EMBO. J.* 8:1403–1408.
41. Pollok K E, Y-J Kim, Z Zhou, J Hurtado, K K Kim, and B S Kwon. 1993. The inducible T cell antigen 4-1BB: Analysis of expression and function. *J Immunol* 150:771.
42. *Antibody Lab Manual*. 1988. Editors are E Harlow and D Lane. Cold Spring Harbor Lab.
43. Pelchen-Matthews, A, J E Armes, G Griffiths, and M Marsh. 1991. Differential endocytosis of CD4 in lymphocytic and nonlymphocytic cells. *J Exp Med.* 173:575.
44. Biffen, M, D McMichael-Phillips, T Larson, A Venkitaraman, and D Alexander. 1994. The CD45 tyrosine phosphatase regulates specific pools of antigen receptor-associated $P_{59}$ and CD4-associated $p56^{lck}$ tyrosine kinases in human T-cells. *EMBO J.* 13:1920.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A method of treating cancerous tumors such that said cancerous tumors are reduced, comprising the administration of a first effective amount of anti-H4-1BB antibody such that said antibody comes into contact with at least one T-cell, and the administration of a second stimulatory molecule such that the molecule also comes into contact with said T-cell.

2. The method of claim 1, wherein said immunostimulatory molecule is selected from the group consisting of:
   a) an anti-CD3 antibody;
   b) an anti-CD28 antibody;
   c) the CD28 protein.

3. The method of claim 1 wherein said anti-H4-1BB antibody is administered at a dosage range equivalent to or greater than 2.0 $\mu$mol to 8.0 $\mu$mol, one to three times per day, and wherein said secondary stimulatory molecule is administered at a dosage range equivalent to or greater than 0.10 $\mu$mol to 2.0 $\mu$mol, one to three times per day.

4. The method of claim 1 wherein the anti-H4-1BB antibody activates the T-cell.

5. The method of claim 1 wherein the anti-H4-1BB antibody enhances T-cell proliferation.

6. The method of claim 1 wherein the anti-H4-1BB antibody induces the proliferation of the T-cell.

7. The method of claim 1 wherein the anti-H4-1BB antibody is a monoclonal antibody.

8. The method of claim 7 wherein the antibody is one secreted by a hybridoma deposited at the American Type Culture Collection under Accession No. HB-11860.

* * * * *

SEQUENCE LISTING

<160> NUMBER OF SEQ ID NOS: 10

<210> SEQ ID NO 1
<211> LENGTH: 838
<212> TYPE: DNA
<213> ORGANISM: Homo sapiens

<400> SEQUENCE: 1

```
aatcagcttt gctagtatca tacctgtcgc agatttcatc atgggaaaca gctgttacaa      60
catagtagcc actctgttgc tggtcctcaa ctttgagagg acaagatcat tgcaggatcc     120
ttgtagtaac tgcccagctg gtacattctg tgataataac aggaatcaga tttgcagtcc     180
ctgtcctcca aatagtttct ccagcgcagg tggacaaagg acctgtgaca tatgcaggca     240
gtgtaaaggt gttttcagga ccaggaagga gtgttcctcc accagcaatg cagagtgtga     300
ctgcactcca gggtttcact gcctgggggc aggatgcagc atgtgtgaac aggattgtag     360
acaaggtcaa gaactgacaa aaaaaggttg taaagactgt tgctttggga catttaacga     420
tcagaaacgt ggcatctgtc gaccctggac aaactgttct ttggatggaa agtctgtgct     480
tgtgaatggg acgaaggaga gggacgtggt ctgtggacca tctccagccg acctctctcc     540
gggagcatcc tctgtgaccc cgcctgcccc tgcgagagag ccaggacact ctccgcagat     600
catctccttc tttcttgcgc tgacgtcgac tgcgttgctc ttcctgctgt tcttcctcac     660
gctccgtttc tctgttgtta aacggggcag aaagaaactc ctgtatatat tcaaacaacc     720
atttatgaga ccagtacaaa ctactcaaga ggaagatggc tgtagctgcc gatttccaga     780
agaagaagaa ggaggatgtg aactgtgaaa tggaagtcaa tagggctgtt gggactttt          838
```

<210> SEQ ID NO 2
<211> LENGTH: 255
<212> TYPE: PRT
<213> ORGANISM: Homo sapiens

<400> SEQUENCE: 2

```
Met Gly Asn Ser Cys Tyr Asn Ile Val Ala Thr Leu Leu Leu Val Leu
 1               5                  10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80
```

-continued

```
Thr Ser Asn Ala Glu Cys Asp Cys Thr Pro Gly Phe His Cys Leu Gly
                85                  90                  95
Ala Gly Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
        115                 120                 125
Lys Arg Gly Ile Cys Arg Pro Trp Thr Asn Cys Ser Leu Asp Gly Lys
    130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
            180                 185                 190
Ala Leu Thr Ser Thr Ala Leu Leu Phe Leu Leu Phe Phe Leu Thr Leu
        195                 200                 205
Arg Phe Ser Val Val Lys Arg Gly Arg Lys Lys Leu Leu Tyr Ile Phe
    210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255
```

<210> SEQ ID NO 3
<211> LENGTH: 20
<212> TYPE: DNA
<213> ORGANISM: Homo sapiens

<400> SEQUENCE: 3
ttytgymgaa artayaaycc           20

<210> SEQ ID NO 4
<211> LENGTH: 20
<212> TYPE: DNA
<213> ORGANISM: Homo sapiens

<400> SEQUENCE: 4
ttytcstsca htggtggaca           20

<210> SEQ ID NO 5
<211> LENGTH: 20
<212> TYPE: DNA
<213> ORGANISM: Homo sapiens

<400> SEQUENCE: 5
cccargswrc aggtyttrca           20

<210> SEQ ID NO 6
<211> LENGTH: 20
<212> TYPE: DNA
<213> ORGANISM: Homo sapiens

<400> SEQUENCE: 6
ttytgrtcrt traatgttcc           20

<210> SEQ ID NO 7
<211> LENGTH: 25
<212> TYPE: DNA
<213> ORGANISM: Homo sapiens

```
<400> SEQUENCE: 7
aataagcttt gctagtatca tacct                                              25

<210> SEQ ID NO 8
<211> LENGTH: 30
<212> TYPE: DNA
<213> ORGANISM: Homo sapiens

<400> SEQUENCE: 8
ttaagatctc tgcggagagt gtcctggctc                                         30

<210> SEQ ID NO 9
<211> LENGTH: 24
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Xaa=Any amino acid

<400> SEQUENCE: 9

Cys Xaa Xaa Cys Xaa Xaa Xaa Xaa Xaa Xaa Xaa Xaa Cys Xaa Xaa
 1               5                  10                  15

Xaa His Xaa Xaa Xaa Cys Xaa Cys
            20

<210> SEQ ID NO 10
<211> LENGTH: 18
<212> TYPE: PRT
<213> ORGANISM: Homo sapiens

<400> SEQUENCE: 10

Phe Glu Arg Thr Arg Ser Leu Gln Asp Pro Cys Ser Asn Cys Pro Ala
 1               5                  10                  15

Gly Thr
```